US008679032B2

(12) United States Patent
Mark et al.

(10) Patent No.: US 8,679,032 B2
(45) Date of Patent: Mar. 25, 2014

(54) VACUUM ASSISTED BIOPSY NEEDLE SET

(71) Applicant: Suros Surgical Systems, Inc., Indianapolis, IN (US)

(72) Inventors: Joseph L. Mark, Indianapolis, IN (US); Michael E. Miller, Trafalgar, IN (US); Michael Hoffa, Brownsburg, IN (US); Zachary R. Nicoson, Indianapolis, IN (US); Terry D. Hardin, Indianapolis, IN (US); Inderjeet S. Jarial, Carmel, IN (US); William O. Hodge, Greenfield, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 0 days.

(21) Appl. No.: 13/743,608

(22) Filed: Jan. 17, 2013

(65) Prior Publication Data

US 2013/0197394 A1 Aug. 1, 2013

Related U.S. Application Data

(63) Continuation of application No. 11/389,274, filed on Mar. 24, 2006, now Pat. No. 8,357,103, which is a continuation-in-part of application No. 10/964,959, filed on Oct. 14, 2004, now Pat. No. 7,390,306.

(60) Provisional application No. 60/510,866, filed on Oct. 14, 2003.

(51) Int. Cl.
*A61B 10/02* (2006.01)

(52) U.S. Cl.
CPC ......... *A61B 10/0266* (2013.01); *A61B 10/0283* (2013.01)
USPC ....................................... 600/566

(58) Field of Classification Search
USPC ................................. 600/566, 565
See application file for complete search history.

(56) References Cited

U.S. PATENT DOCUMENTS

| 2,472,116 A | 6/1949 | Maynes |
| 2,660,342 A | 11/1953 | Ruf |

(Continued)

FOREIGN PATENT DOCUMENTS

| CH | SU 1551362 | 1/1987 |
| DE | 1160573 | 1/1964 |

(Continued)

OTHER PUBLICATIONS

PCT International Search Report PCT/IB2007/050975 dated Nov. 21, 2007.

(Continued)

*Primary Examiner* — Sean Dougherty
*Assistant Examiner* — Michael C Stout
(74) *Attorney, Agent, or Firm* — Vista IP Law Group LLP

(57) ABSTRACT

A biopsy device having a cutting element is disclosed. The cutting element includes an inner cannula having a tissue receiving aperture disposed proximate a distal end thereof and an inner lumen. The inner cannula is slidably disposed within the inner lumen of an outer cannula. A vacuum chamber is disposed about at least a portion of the cutting element and is configured to create a vacuum in the cutting element during a biopsy procedure. The inner cannula is advanced distally outwardly and to cause the vacuum to be generated in the vacuum chamber. The vacuum is delivered to the cutting element whereby tissue is drawn into the tissue receiving aperture. The outer cannula is advanced distally outwardly after the inner cannula such that tissue drawn into the tissue cutting aperture is severed.

10 Claims, 29 Drawing Sheets

(56) References Cited

U.S. PATENT DOCUMENTS

| | | | |
|---|---|---|---|
| 2,735,427 A | 2/1956 | Sullivan | |
| 2,863,452 A | 12/1958 | Ogle, Sr. | |
| 2,892,457 A | 6/1959 | Sturtz | |
| 3,477,423 A | 11/1969 | Griffith | |
| 3,517,688 A | 6/1970 | Scholle | |
| 3,561,429 A | 2/1971 | Jewett et al. | |
| 3,819,091 A | 6/1974 | Hollender | |
| 3,844,272 A | 10/1974 | Banko | |
| 3,905,365 A | 9/1975 | Colombo | |
| 4,301,802 A | 11/1981 | Poler | |
| 4,461,305 A | 7/1984 | Cibley | |
| 4,570,632 A | 2/1986 | Woods | |
| 4,594,073 A | 6/1986 | Stine | |
| 4,600,014 A | 7/1986 | Beraha | |
| 4,605,011 A | 8/1986 | Naslund | |
| 4,667,684 A | 5/1987 | Leigh | |
| 4,697,600 A * | 10/1987 | Cardenas et al. | 600/566 |
| 4,699,154 A | 10/1987 | Lindgren | |
| 4,708,147 A | 11/1987 | Haaga | |
| 4,711,250 A | 12/1987 | Gilbaugh, Jr. et al. | |
| 4,733,671 A | 3/1988 | Mehl | |
| 4,735,215 A | 4/1988 | Goto et al. | |
| 4,747,414 A | 5/1988 | Brossel | |
| 4,776,346 A | 10/1988 | Beraha et al. | |
| 4,776,840 A | 10/1988 | Freitas et al. | |
| 4,781,700 A | 11/1988 | Vicario | |
| 4,817,631 A | 4/1989 | Schnepp-Pesch et al. | |
| 4,881,551 A | 11/1989 | Taylor | |
| 4,893,635 A | 1/1990 | de Groot et al. | |
| 4,907,598 A | 3/1990 | Bauer | |
| 4,950,265 A | 8/1990 | Taylor | |
| 4,982,739 A | 1/1991 | Hemstreet et al. | |
| 4,989,614 A | 2/1991 | Dejter, Jr. et al. | |
| 5,019,036 A | 5/1991 | Stahl | |
| 5,025,797 A * | 6/1991 | Baran | 600/567 |
| 5,048,538 A | 9/1991 | Terwelliger et al. | |
| 5,127,419 A | 7/1992 | Kaldany | |
| 5,133,360 A | 7/1992 | Spears | |
| 5,159,933 A | 11/1992 | Hut | |
| 5,172,701 A * | 12/1992 | Leigh | 600/566 |
| 5,183,052 A | 2/1993 | Terwilliger | |
| 5,188,118 A | 2/1993 | Terwilliger | |
| 5,213,110 A * | 5/1993 | Kedem et al. | 600/567 |
| 5,220,926 A | 6/1993 | Jones | |
| 5,224,470 A * | 7/1993 | Schnepp-Pesch et al. | 600/566 |
| 5,246,011 A | 9/1993 | Caillouette | |
| 5,249,582 A | 10/1993 | Taylor | |
| 5,281,197 A | 1/1994 | Arias et al. | |
| 5,282,476 A | 2/1994 | Terwilliger | |
| 5,289,831 A | 3/1994 | Bosley | |
| 5,348,022 A | 9/1994 | Leigh et al. | |
| 5,374,252 A | 12/1994 | Banks et al. | |
| 5,400,798 A * | 3/1995 | Baran | 600/567 |
| 5,425,376 A * | 6/1995 | Banys et al. | 600/566 |
| 5,469,860 A | 11/1995 | De Santis | |
| 5,492,130 A * | 2/1996 | Chiou | 600/566 |
| 5,505,211 A | 4/1996 | Ohto et al. | |
| 5,511,556 A | 4/1996 | DeSantis | |
| 5,526,822 A | 6/1996 | Burbank et al. | |
| 5,535,755 A | 7/1996 | Heske | |
| 5,546,957 A | 8/1996 | Heske | |
| 5,560,373 A * | 10/1996 | De Santis | 600/566 |
| 5,649,547 A | 7/1997 | Ritchart et al. | |
| 5,769,086 A * | 6/1998 | Ritchart et al. | 600/566 |
| 5,775,333 A | 7/1998 | Burbank et al. | |
| 5,797,907 A | 8/1998 | Clement | |
| 5,817,033 A | 10/1998 | DeSantis et al. | |
| 5,928,164 A | 7/1999 | Burbank et al. | |
| 5,944,673 A | 8/1999 | Gregoire et al. | |
| 5,971,939 A * | 10/1999 | DeSantis et al. | 600/562 |
| 5,980,469 A | 11/1999 | Burbank et al. | |
| 5,980,545 A | 11/1999 | Pacala et al. | |
| 5,993,399 A | 11/1999 | Pruitt et al. | |
| 6,017,316 A | 1/2000 | Ritchart et al. | |
| 6,019,733 A | 2/2000 | Farascioni | |
| 6,050,955 A * | 4/2000 | Bryan et al. | 600/566 |
| 6,059,807 A | 5/2000 | Boudjema | |
| 6,142,955 A | 11/2000 | Farascioni et al. | |
| 6,155,989 A * | 12/2000 | Collins | 600/565 |
| 6,161,034 A | 12/2000 | Burbank et al. | |
| 6,193,673 B1 | 2/2001 | Viola et al. | |
| 6,251,418 B1 | 6/2001 | Ahern et al. | |
| 6,258,064 B1 | 7/2001 | Smith et al. | |
| 6,280,399 B1 | 8/2001 | Rossin et al. | |
| 6,347,241 B2 | 2/2002 | Burbank et al. | |
| 6,358,217 B1 | 3/2002 | Bourassa | |
| 6,387,057 B1 | 5/2002 | Heske | |
| 6,419,641 B1 | 7/2002 | Mark et al. | |
| 6,428,486 B2 | 8/2002 | Ritchart et al. | |
| 6,436,054 B1 | 8/2002 | Viola et al. | |
| 6,488,636 B2 | 12/2002 | Bryan et al. | |
| 6,494,844 B1 | 12/2002 | Van Bladel et al. | |
| 6,506,165 B1 * | 1/2003 | Sweeney | 600/562 |
| 6,514,215 B1 * | 2/2003 | Ouchi | 600/564 |
| 6,551,255 B2 | 4/2003 | Van Bladel et al. | |
| 6,554,778 B1 | 4/2003 | Fleming, III | |
| 6,554,779 B2 | 4/2003 | Viola et al. | |
| 6,572,563 B2 | 6/2003 | Ouchi | |
| 6,589,240 B2 | 7/2003 | Hinchliffe | |
| 6,592,530 B1 | 7/2003 | Farhadi | |
| 6,626,868 B1 | 9/2003 | Prestidge et al. | |
| 6,702,760 B2 | 3/2004 | Krause et al. | |
| 6,712,773 B1 | 3/2004 | Viola | |
| 6,725,083 B1 | 4/2004 | Burbank et al. | |
| 6,863,676 B2 | 3/2005 | Lee et al. | |
| 6,942,627 B2 | 9/2005 | Huitema | |
| 6,997,926 B2 | 2/2006 | Gellman | |
| 7,278,970 B2 | 10/2007 | Goldenberg | |
| 7,390,306 B2 | 6/2008 | Mark | |
| 7,608,048 B2 | 10/2009 | Goldenberg | |
| 8,162,850 B2 | 4/2012 | Parihar et al. | |
| 2002/0111563 A1 | 8/2002 | Hall | |
| 2003/0018281 A1 | 1/2003 | Huitema | |
| 2003/0125639 A1 | 7/2003 | Fisher et al. | |
| 2003/0153874 A1 | 8/2003 | Tal | |
| 2003/0195436 A1 | 10/2003 | Van Bladel et al. | |
| 2003/0229293 A1* | 12/2003 | Hibner et al. | 600/567 |
| 2004/0097830 A1* | 5/2004 | Cooke et al. | 600/564 |
| 2004/0158172 A1 | 8/2004 | Hancock | |
| 2004/0162572 A1* | 8/2004 | Sauer | 606/170 |
| 2004/0230133 A1 | 11/2004 | Miller et al. | |
| 2005/0027210 A1 | 2/2005 | Miller | |
| 2005/0054947 A1 | 3/2005 | Goldenberg | |
| 2005/0075580 A1 | 4/2005 | Leigh et al. | |
| 2005/0080355 A1 | 4/2005 | Mark | |
| 2005/0165328 A1* | 7/2005 | Heske et al. | 600/566 |
| 2005/0203439 A1* | 9/2005 | Heske et al. | 600/566 |
| 2005/0240118 A1 | 10/2005 | Huitema | |
| 2005/0277829 A1 | 12/2005 | Tsonton et al. | |
| 2006/0089565 A1 | 4/2006 | Schramm | |
| 2006/0155210 A1 | 7/2006 | Beckman et al. | |
| 2006/0173377 A1* | 8/2006 | McCullough et al. | 600/566 |
| 2007/0106176 A1 | 5/2007 | Mark et al. | |
| 2008/0200835 A1* | 8/2008 | Monson et al. | 600/567 |
| 2009/0204023 A1 | 8/2009 | Goldenberg | |

FOREIGN PATENT DOCUMENTS

| | | |
|---|---|---|
| DE | 141 108 | 4/1980 |
| DE | 20204363 | 5/2002 |
| EP | 0 010 321 | 4/1980 |
| EP | 0561732 | 9/1993 |
| EP | 1520518 A2 | 4/2005 |
| EP | 1698283 A1 | 9/2006 |
| WO | WO-83/03343 | 10/1983 |
| WO | WO-96/24289 A | 8/1996 |
| WO | WO-97/20504 | 6/1997 |
| WO | WO-02/22023 A1 | 3/2002 |

(56) References Cited

FOREIGN PATENT DOCUMENTS

| WO | WO 03/009766 A1 | 2/2003 |
|---|---|---|
| WO | WO-2005/037106 A | 4/2005 |
| WO | WO-2005/063126 A | 7/2005 |
| WO | WO-2006/083770 A2 | 8/2006 |
| WO | WO-2008/106583 A1 | 9/2008 |

OTHER PUBLICATIONS

Response to Final Office Action dated Jun. 8, 2011 for U.S. Appl. No. 12/124,949.
Notice of Allowance dated Mar. 8, 2011 for U.S. Appl. No. 12/039,364.
Final Office Action dated Jun. 8, 2011 for U.S. Appl. No. 12/124,949.
Final Office action dated Oct. 26, 2010 for U.S. Appl. No. 12/124,949.
Publication in OBGYN,net entitled "Minimally Invsive Surgery Products for General Surgery Continue to Provide Opportunities for Innovative Manufacturers" by Keith Hammond, dated Apr. 22, 1998.
International Search Report No. PCT/US2004/033909 dated May 18, 2005.
Non-Final Office Action dated May 14, 2010 for U.S. Appl. No. 12/124,949.
Response to Non-Final Office Action dated May 14, 2010 for U.S. Appl. No. 12/124,949.
Response to Final Office Action dated Oct. 26, 2010 for U.S. Appl. No. 12/124,949.
Brochure entitled "Interventional MRI", Invivo Corporation Daum Technology; Copyright 2005.
International Search Report for PCT/US2009/049214 dated Sep. 15, 2009.
International Search Report for PCT/US2008/055248 dated Jun. 17, 2008.

* cited by examiner

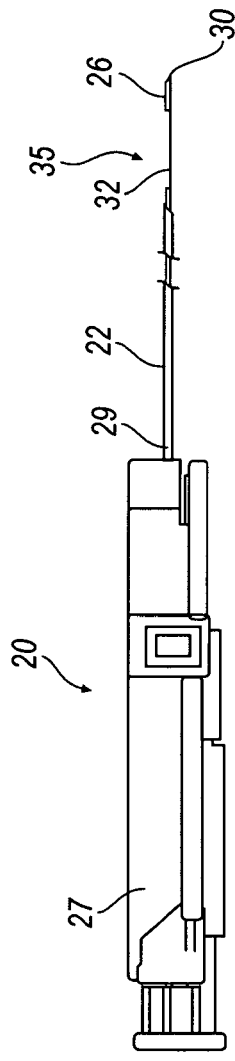
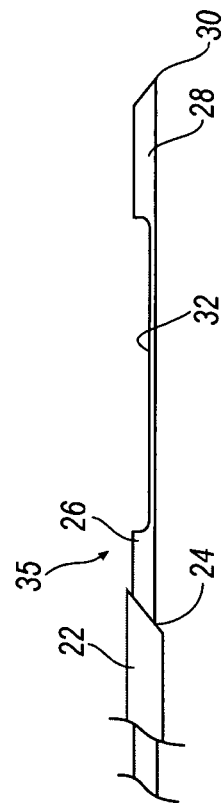
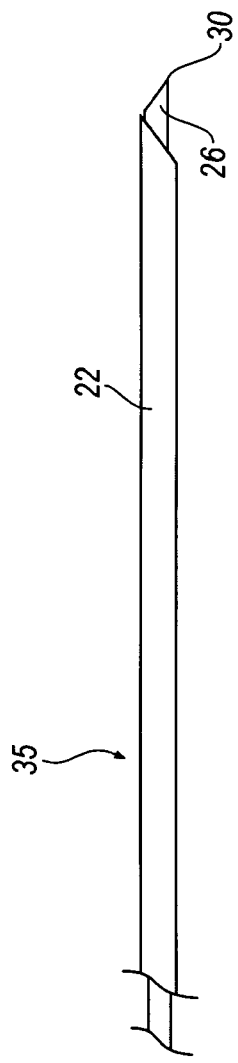
FIG. 1 (PRIOR ART)
FIG. 2 (PRIOR ART)
FIG. 3 (PRIOR ART)

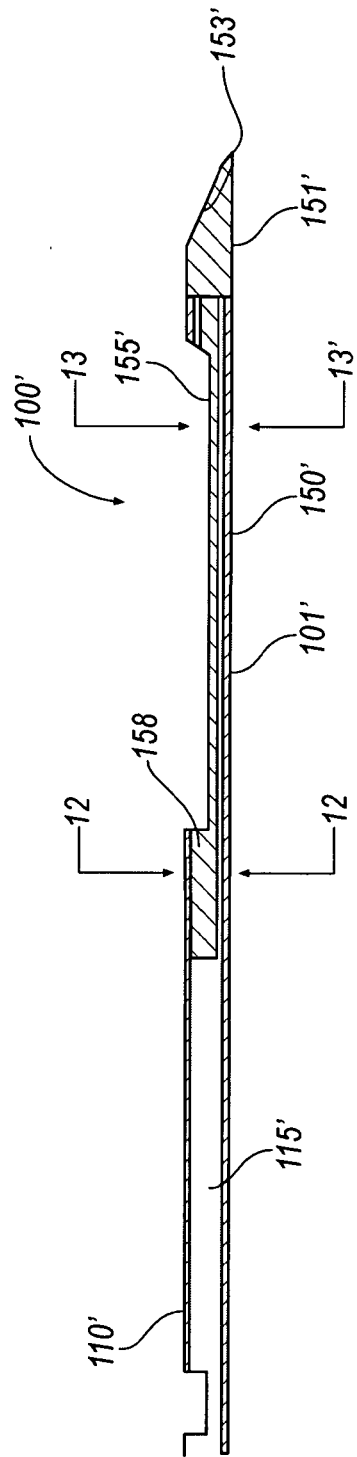
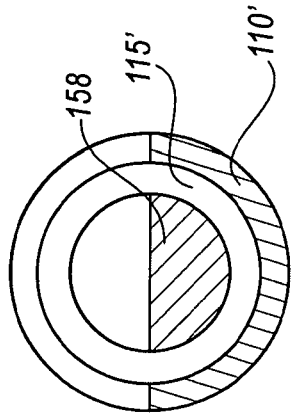
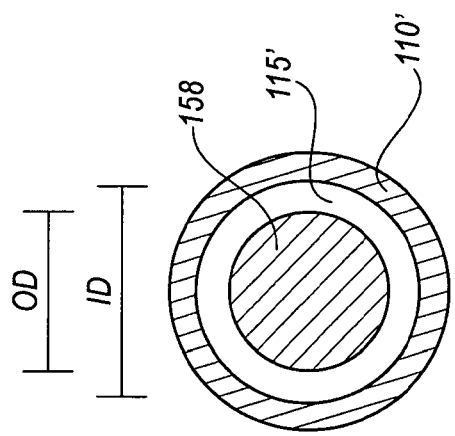

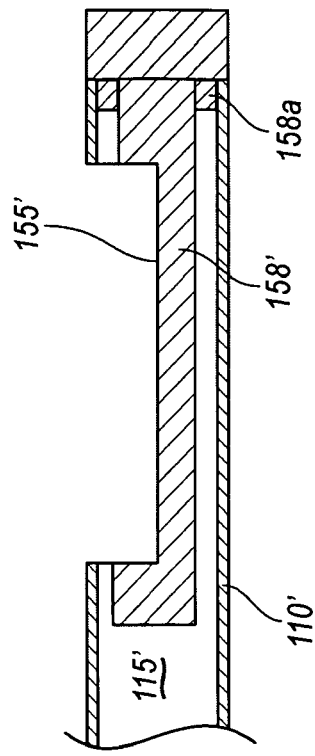
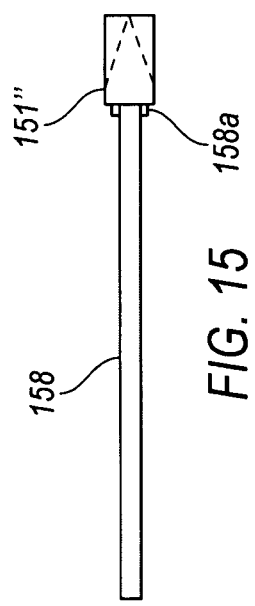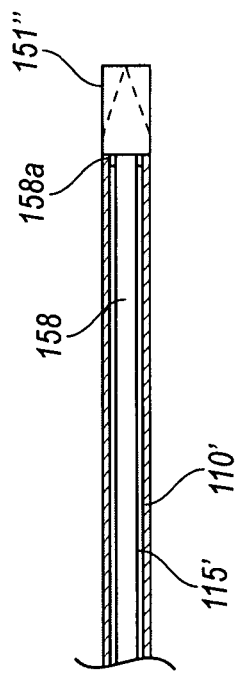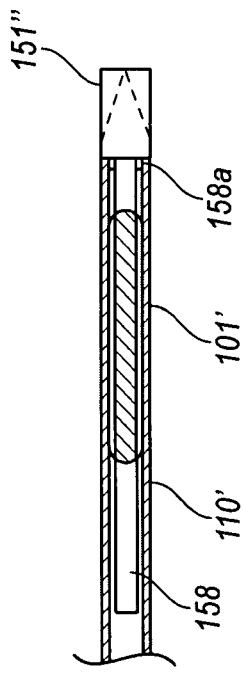

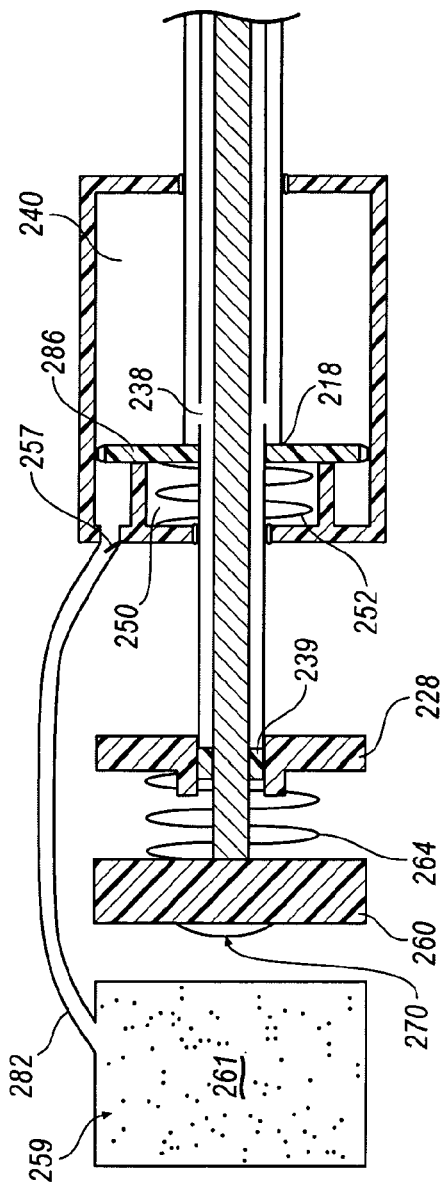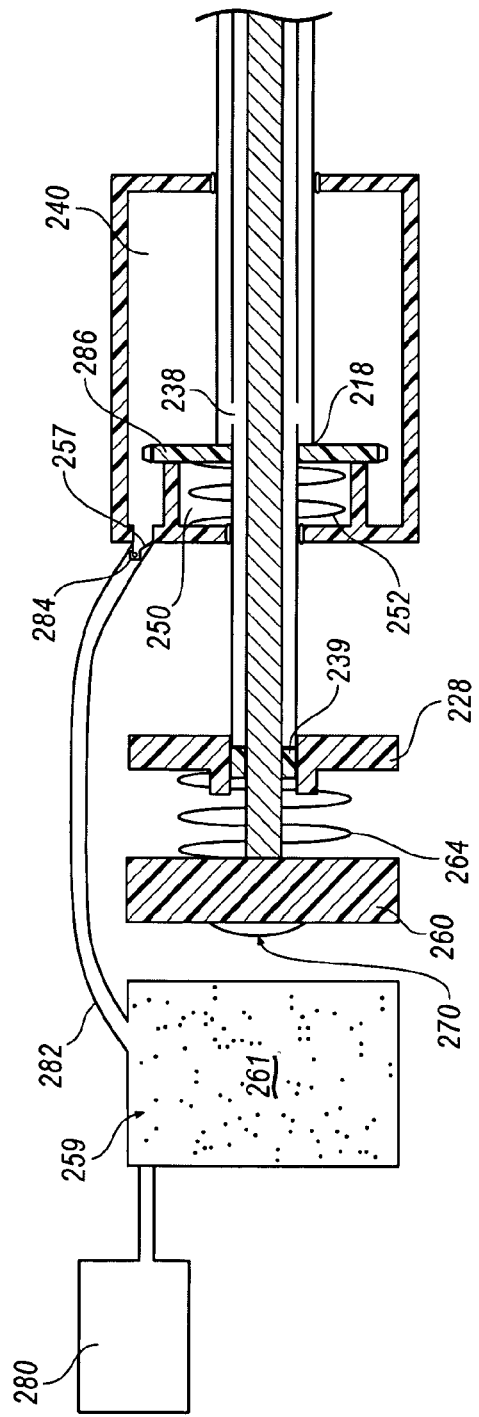
FIG. 27
FIG. 28

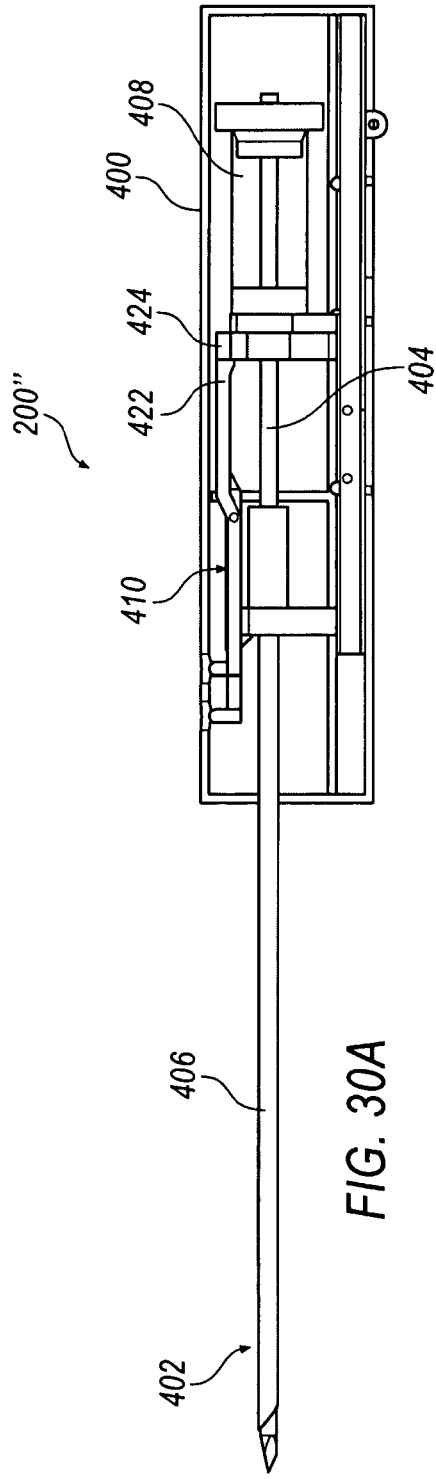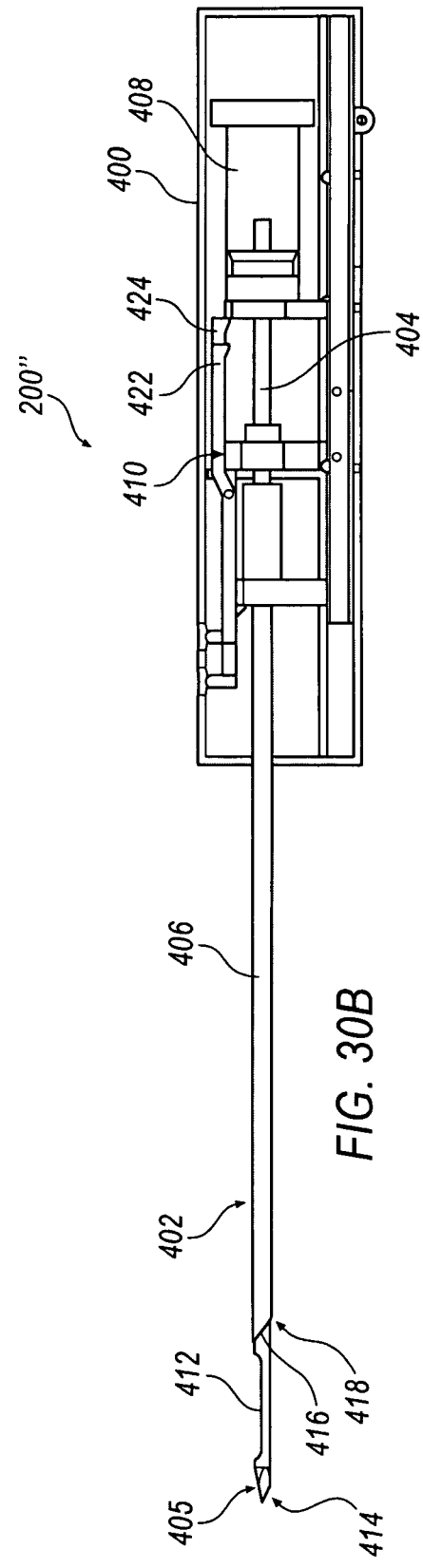
FIG. 30A
FIG. 30B

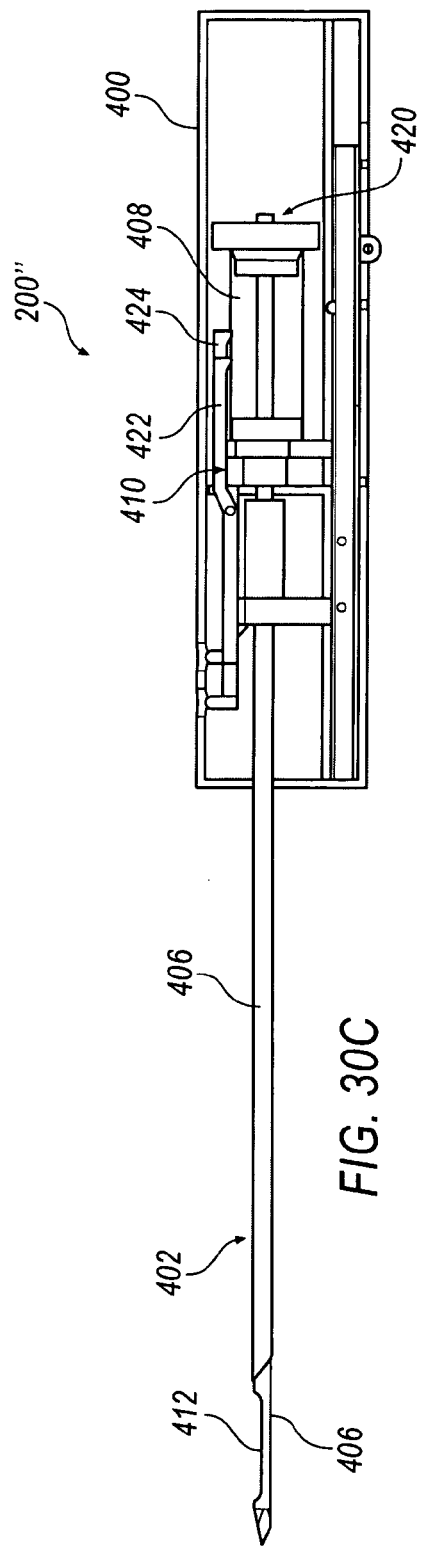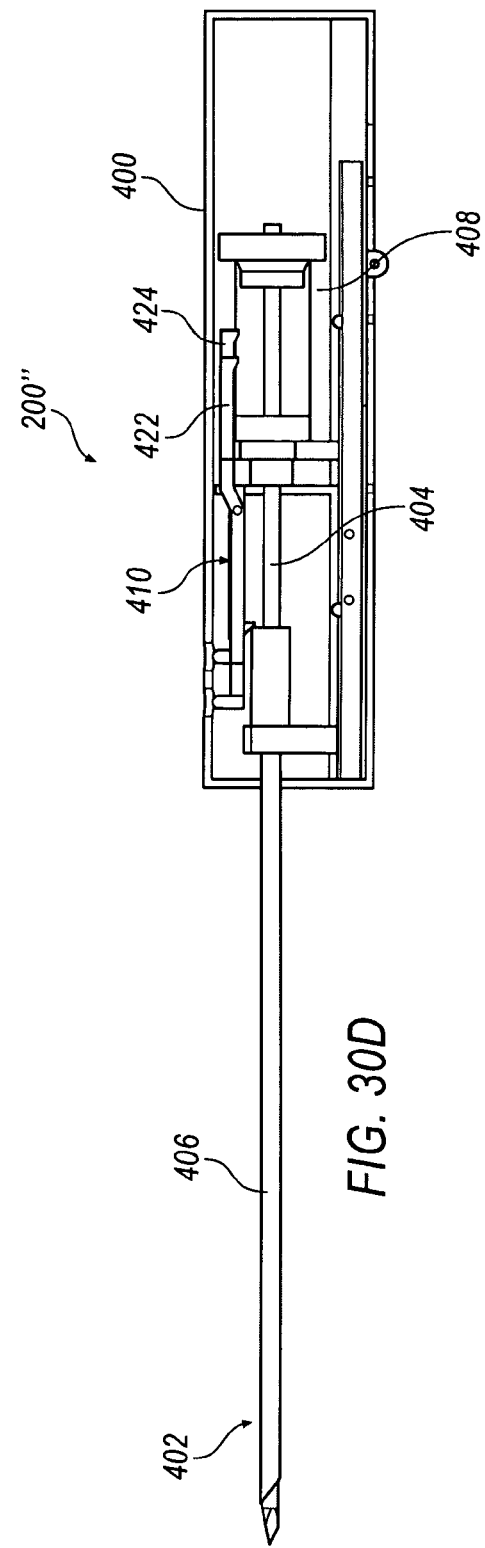

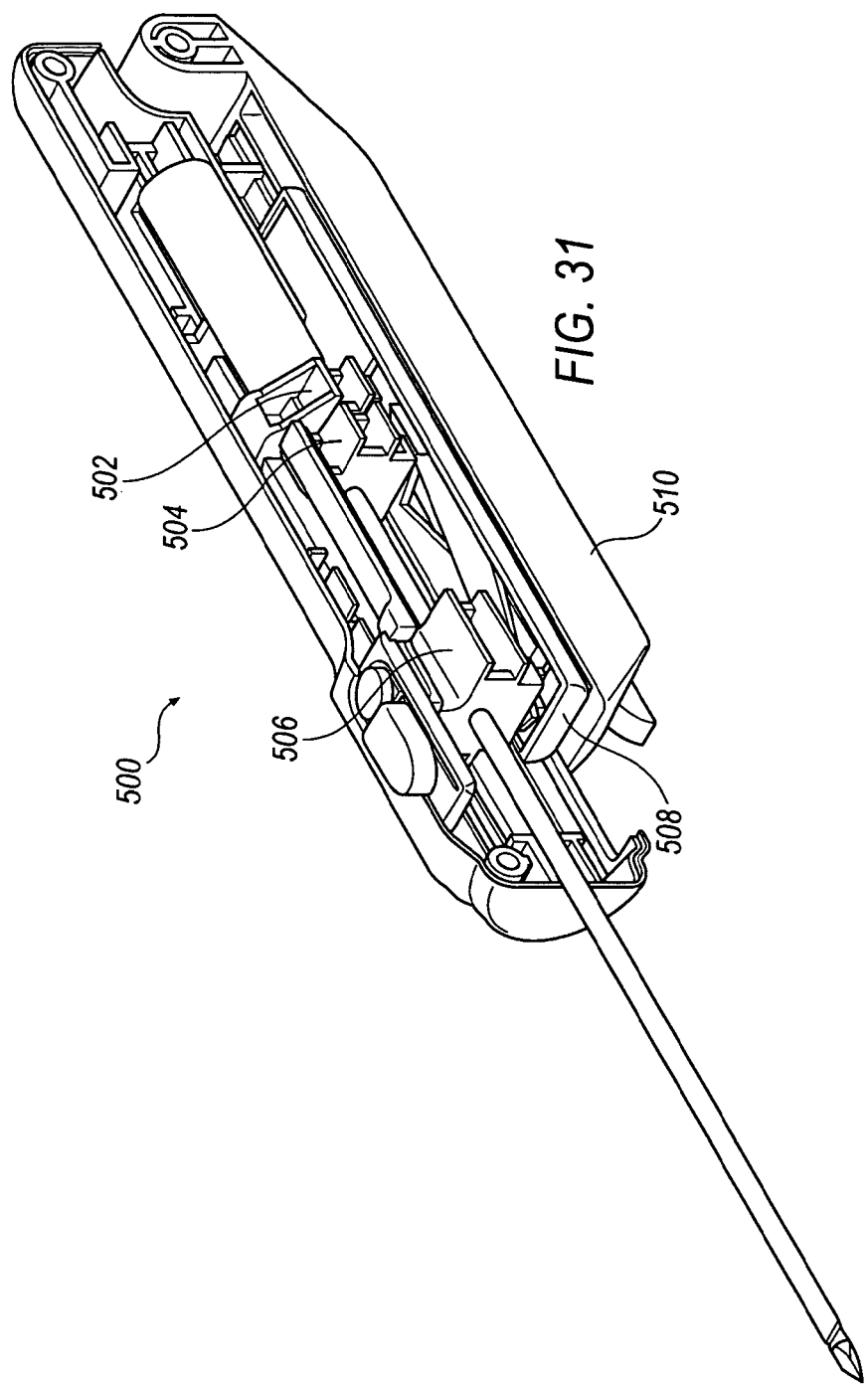

VACUUM ASSISTED BIOPSY NEEDLE SET

CROSS REFERENCE TO RELATED APPLICATIONS

The present application is a continuation of pending U.S. patent application Ser. No. 11/389,274, filed Mar. 24, 2006, which is a continuation-in-part of U.S. patent application Ser. No. 10/964,959, filed Oct. 14, 2004, which claims priority to U.S. provisional patent application Ser. No. 60/510,866, filed on Oct. 14, 2003. The foregoing applications are hereby incorporated by reference into the present application in their entirety.

FIELD OF THE INVENTION

The present invention generally relates to the field of tissue sampling and harvesting. More specifically, the invention relates to biopsy needle sets and devices.

BACKGROUND OF THE INVENTION

In the practice of diagnostic medicine, it is often necessary or desirable to perform a biopsy, or to sample selected tissue from a living patient for medical evaluation. Cytological and histological studies of the biopsy sample can then be performed as an aid to the diagnosis and treatment of disease. Biopsies can be useful in diagnosing and treating various forms of cancer, as well as other diseases in which a localized area of affected tissue can be identified.

Biopsies are routinely performed on tissue using a needle set, which typically includes a stylet with a pointed tip and a notch defined near its distal end. The stylet is slidably disposed within a cannula so that the notch can be alternately exposed or covered. Typically, a hub is connected to the proximal end of each needle. Such needle sets are used with or incorporated in various forms of biopsy devices, such as the single action and double action biopsy devices. One such needle set is incorporated into the single action biopsy device shown in FIGS. 1-4.

Referring to FIGS. 1-4, single action biopsy device 20 includes an outer hollow needle 22 defining a lumen 24 therethrough. A stylet 26 is slidingly disposed within lumen 24 and is moveable relative to outer needle 22. A first or distal end 28 of stylet 26 is provided with a tissue cutting-point 30 and a cavity 32 adjacent to first end 28 for receiving tissue samples. Stylet 26 is slidable relative to outer needle 22 between a first or retracted position (FIG. 3) and a second or extended position (FIG. 2).

In the first position, stylet 26 is retracted within lumen 24 so that outer needle 22 covers cavity 32. In the second position, the first end 28 of stylet 26 is extended away from outer needle 22 to expose cavity 32 to tissues at the biopsy site.

During a biopsy procedure, device 20 will be positioned with the cavity 32 at the targeted site for the biopsy. Stylet 26 is momentarily driven into the tissue far enough to expose cavity 32. Tissue then prolapses into cavity 32. The device is then fired to advance outer needle 22 along stylet 26 to cover cavity 32. This forward movement of outer needle 22 severs the prolapsed tissue to obtain a tissue sample, which becomes trapped in cavity 32 of stylet 26. With outer needle 22 blocking the opening of cavity 32, biopsy device 20 is then withdrawn from the target site, carrying the sample within cavity 32. To collect the biopsy sample, outer needle 22 is once again retracted to expose cavity 32 of stylet 26. The procedure may be repeated several times until satisfactory samples have been obtained.

The firing mechanism 40 for such known single action biopsy devices is shown in FIG. 4. Firing mechanism 40 includes a housing 27 having finger grips 41 and 42. An actuator 43 is operatively engaged with both the stylet 26 and outer needle 22. Actuator 43 includes a gripping portion 44 and a drive mechanism 45. Drive mechanism 45 operates to depress a drive carriage 46 against the action of a spring 35. Housing 27 includes a resilient latch 36 that engages an underside 47 of the carriage 46 in the retracted position. Latch 36 is released by forward movement of the drive mechanism 45 so that the spring 35 urges carriage 46 outwardly, which in turn thrusts outer needle 22 over the sampling cavity 32 of the stylet 26. Cover 49 snap-fits over housing 27 to protect spring 35 and the sliding engagement between carriage 46 and housing 27 from debris and interference.

Double action biopsy devices also employ similar needle sets. In a double action biopsy device, movement of inner and outer needles 26, 22 to capture a sample occurs almost instantaneously by means of a firing mechanism engaged with proximal ends 29 of needles 26, 22. A double action biopsy device is disclosed in U.S. Pat. No. 5,538,010.

While these single and double action biopsy devices are widely used, a basic problem remains in the field of biopsy, which is the need to obtain a sufficient amount of sample tissue. One potential cause of the problem is that as the outer needle passes over the tissue cavity, the outer needle has a tendency to push the tissue away from the cavity. This results in samples that are inferior in quality or too small, which precludes the pathologist from conclusively determining whether disease is present, and if so, to what extent it has progressed. The pathologist must then issue an inconclusive diagnostic report. This causes the physician to recall the patient and attempt another needle biopsy, or in some situations, the patient is scheduled for a more invasive, traumatic and expensive procedure such as an open surgical biopsy.

The challenge has been to consistently obtain sufficient tissue volume and quality tissue cores, regardless of tissue type, to meet the needs of the pathologist so that a conclusive diagnosis can be achieved. Therefore, a need remains for a device that can consistently achieve this result.

SUMMARY

An embodiment of a biopsy device having a cutting element is disclosed. The cutting element includes an outer cannula having a tissue receiving aperture disposed proximate a distal end thereof and an inner lumen. An inner cannula is slidably disposed within the inner lumen of the outer cannula. The inner cannula also has an inner lumen and includes an open distal end defined by a sharpened circumferential edge. A vacuum chamber is disposed about at least a portion of the cutting element and is configured to create a vacuum in the cutting element during a biopsy procedure. The outer cannula is advanced distally outwardly to cause the vacuum to be generated in the vacuum chamber and delivered to the cutting element whereby tissue is drawn into the tissue receiving aperture. The inner cannula is then advanced distally outwardly after the outer cannula such that tissue drawn into the tissue cutting aperture is severed.

In an alternative embodiment of the biopsy device, a trigger operates to first cause the inner cannula to be advanced distally outwardly and to cause a vacuum to be generated such that tissue is drawn into a tissue receiving aperture formed in the inner cannula. Thereafter, the outer cannula is advanced distally outwardly such that tissue drawn into the tissue receiving aperture is severed.

In at least one other embodiment of the biopsy device, a vacuum bed is formed at the distal end of the inner cannula for providing a uniform vacuum throughout the tissue receiving aperture. A trocar blank is inserted into the distal end of the inner cannula which is then ground or machined to form the vacuum bed. The vacuum bed includes at least one vacuum channel or aperture which operates to uniformly distributes vacuum air over the entire vacuum bed.

BRIEF DESCRIPTION OF DRAWINGS

FIG. 1 is a side elevational view of a prior art biopsy device;

FIG. 2 is an enlarged fragmentary view of the device of FIG. 1, showing details of the tip of the device when in an extended position;

FIG. 3 is an enlarged fragmentary view of the device of FIG. 1 showing details of the tip of the device when in a retracted position;

FIG. 11 is a side sectional view of the distal end of another embodiment of a needle set;

FIG. 12 is a cross sectional view of the needle set of FIG. 11 taken along line 12-12 of FIG. 11.

FIG. 13 is a cross sectional view of the needle set of FIG. 11 taken along line 13-13.

FIGS. 15-17B show the construction of the inner member of FIG. 7;

FIG. 27 is a partial cross-sectional view of another embodiment of a double-action biopsy device of FIG. 25.

FIG. 28 is a partial cross-sectional view of yet another embodiment of a double-action biopsy device of FIG. 25.

FIGS. 30A-30D are cross-sectional views of a fourth alternative embodiment of a double-action biopsy device and;

FIG. 31 illustrates a prespective view with a partially remove housing exposing an actuating platform.

Figure 4:
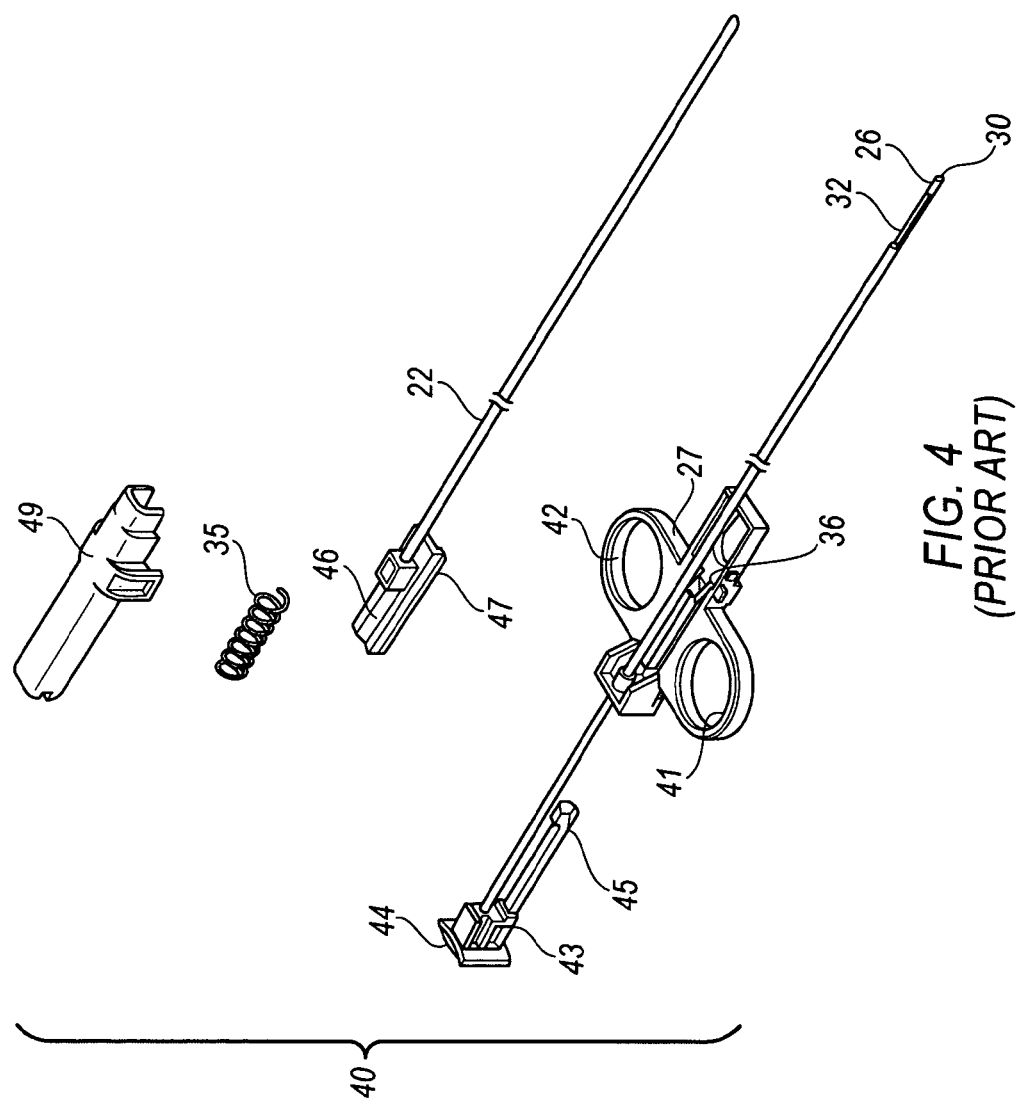
FIG. 4 is an exploded view of the device of FIGS. 1-3.

Although the drawings represent embodiments of the present invention, the drawings are not necessarily to scale and certain features may be exaggerated in order to better illustrate and explain the present invention. The exemplification set out herein illustrates certain embodiments of the invention, in one, or more forms, and such exemplifications are not to be construed as limiting the scope of the invention in any manner.

DETAILED DESCRIPTION

For the purposes of promoting an understanding of the principles of the invention, reference will now be made to the embodiments illustrated in the drawings and specific language will be used to describe the same. It will nevertheless be understood that no limitation of the scope of the invention is thereby intended. The invention includes any alterations and further modifications in the illustrated devices and described methods and further applications of the principles of the invention that would normally occur to one skilled in the art to which the invention relates.

The terms proximal and distal as used herein will be understood to describe opposite ends of a device or element, and generally will be employed so that proximal is understood as "toward the heart" and distal is understood to mean "away from the heart" or "away from the practitioner" and "toward the practitioner," respectively.

FIGS. 5-10 depict a first embodiment of a needle set 50 for a biopsy device. Needle set 50 includes an inner member 100 slidably disposed within a lumen 58 of an outer member 60. Outer member 60 has a tip member 61 attached to a center portion 70 and a hub member 80 positioned on the proximal end of outer member 60. Tip member 61 has a working end 63 with an opening 63(a) therethrough, an opposite end 64 and a tip lumen 65 defined therebetween. As seen most clearly in FIG. 6, center portion 70 has a first end 71 hermetically connected to the opposite end 64 of the tip member 61 and a second end 73. A center lumen 75 is defined between first and second ends 71 and 73. The center lumen 75 is in fluid communication with the tip lumen 65. Hub member 80 is positioned on the second end 73 of the center portion 70. Hub member 80 defines a hub lumen 85 that is in fluid communication with the center lumen 75. The hub lumen 85 is also in fluid communication with a pair of openings 86a, 87a defined in opposite sides 86, 87 of the hub member 80. A vent seal 88 may be disposed within the hub member 80. The second end 73 of the center portion 70 is attached to hub member 80 at side 86 and positioned so that the center lumen 75 is in substantial alignment with the hub lumen 85.

A seal member 90 may be positioned within the center lumen 75 and fixed to an interior surface of the center lumen 70. The seal member 90 is any suitable seal member, such as for example, an O-ring. Seal member 90 defines an opening 91, which is in communication with the center lumen 75.

Figure 5:
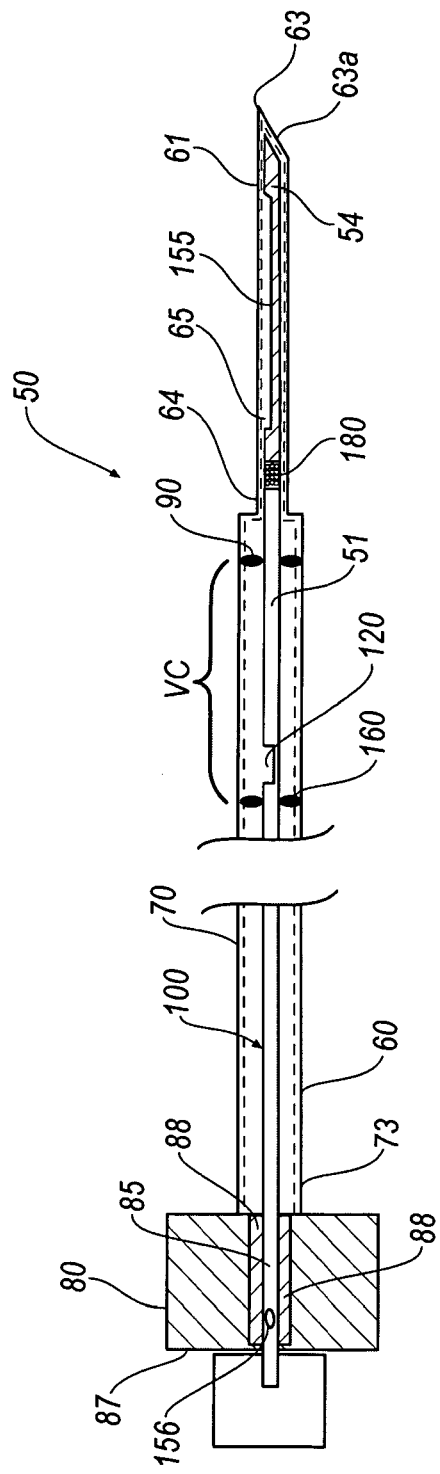
FIG. 5 is a partial sectional view showing a needle set according to an embodiment of the present invention.
Figure 6:
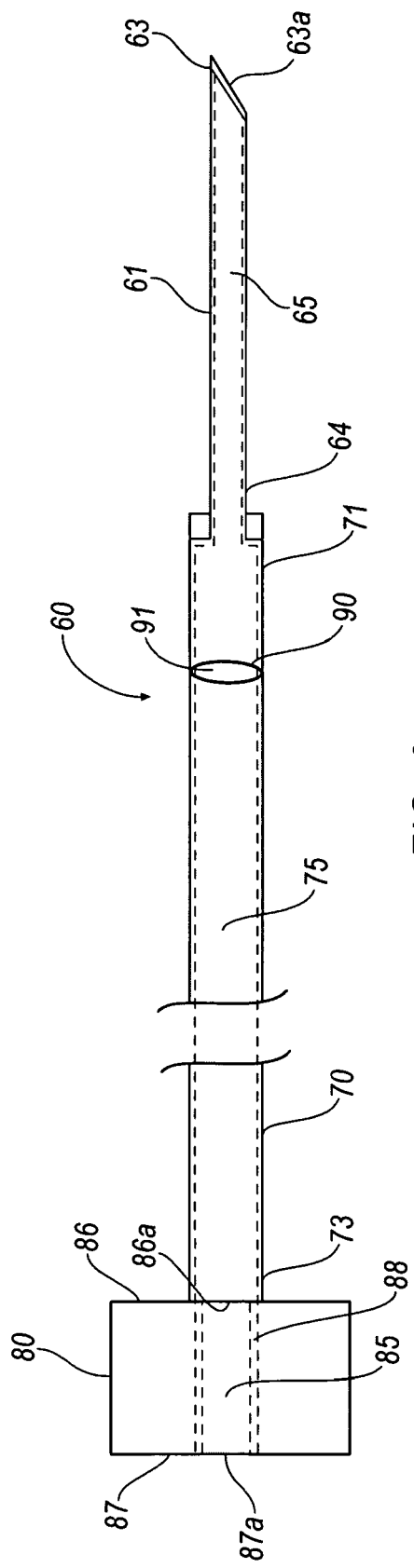
FIG. 6 is a side elevational view of an outer member of the needle set of FIG. 5.
Figure 7:
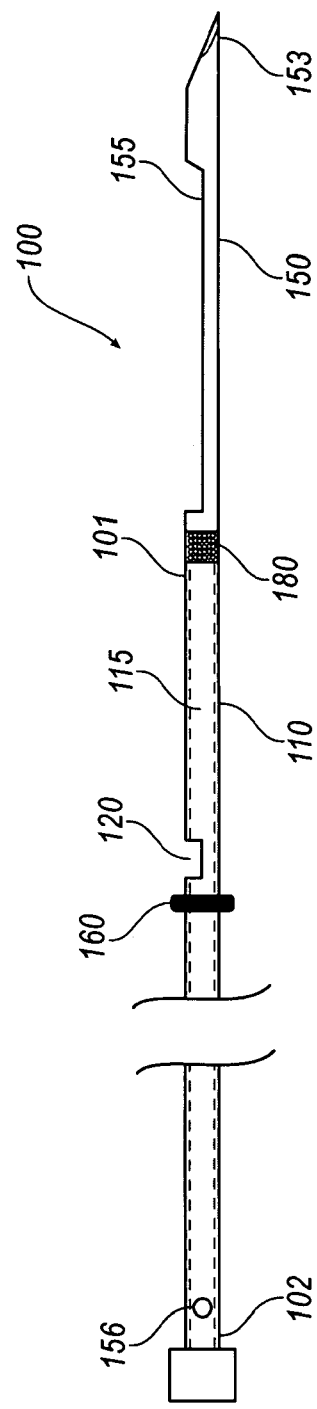
FIG. 7 is a side elevational view of an inner member of the needle set of FIG. 5.

Referring now to FIG. 7, inner member 100 includes a cannula 110 and a sampling portion 150. Cannula 110 may be slidably disposed within the center lumen 75 and through the opening 91 of the seal member 90 as shown in FIG. 5. An inner lumen 115 is defined between distal and proximal ends 101, 102 of cannula 100. Cannula 110 includes an opening 120 and a vent aperture 156 that is positioned adjacent the proximal end 102. Both the opening 120 and vent aperture 156 are formed through the wall of the cannula 110 and are in fluid communication with the inner lumen 115. While opening 120 is shown as a notch, it is understood that opening 120 may take the form of other configurations without departing from the invention.

Sampling portion 150 is attached to the distal end 101 of cannula 110. Sampling portion 150 includes a sampling cavity 155. Sampling portion 150 may also be provided with a tissue piercing tip 153. A cannula seal member 160 is secured to the outer surface of the cannula 110 proximal to the opening 120. Cannula seal member 160 is configured to movably seal within the center lumen 75 of FIG. 6.

Figure 8:
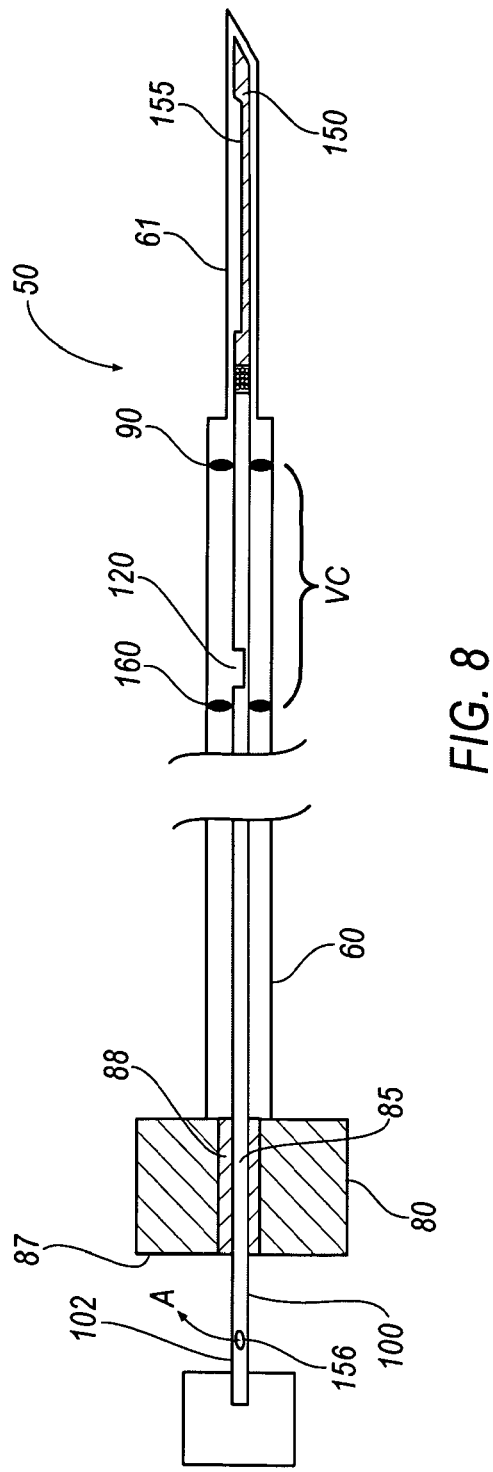
FIG. 8 is a partial side sectional view of the needle set in a retracted position
Figure 9A:
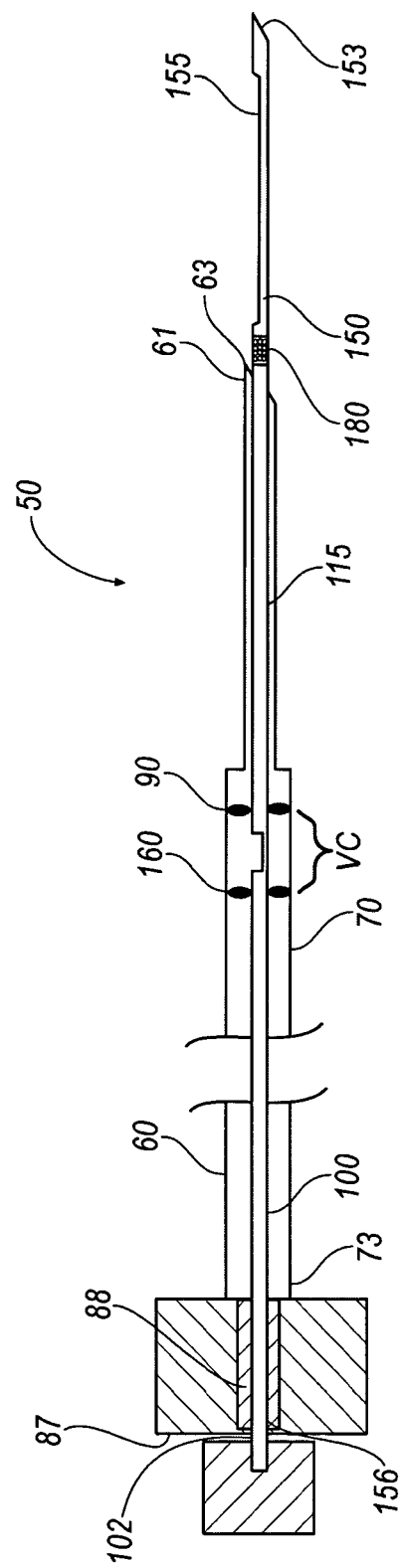
FIGS. 9A and 9B are partial side sectional views of the needle set of FIG. 5 in an extended position.

As shown in FIG. 8, the cannula seal member 160 and the seal member 90 cooperate to define a vacuum chamber VC. The opening 120 may be disposed within the vacuum chamber VC. The inner and outer members 60, 100 are movable relative to one another between a retracted position in which the tip member 61 covers the sampling cavity 155 and the vacuum chamber VC is expanded, and an extended position. The needle set may be placed in a cocked position as shown in FIG. 8 with the vent aperture 156 exposed to vent air A from the inner lumen 115 as the needle set is moved to the extended position (as shown in FIG. 9A) such that movement of the outer member 60 to the distal position generates vacuum which is delivered to the inner lumen 115. In the extended position the sampling portion 150 is extended away from the tip member 61 to expose the sampling cavity 155 and the vacuum chamber VC is contracted. The vent aperture 156 is sealed by the vent seal 88 when the needle set is completely in the extended position.

Figure 9B:
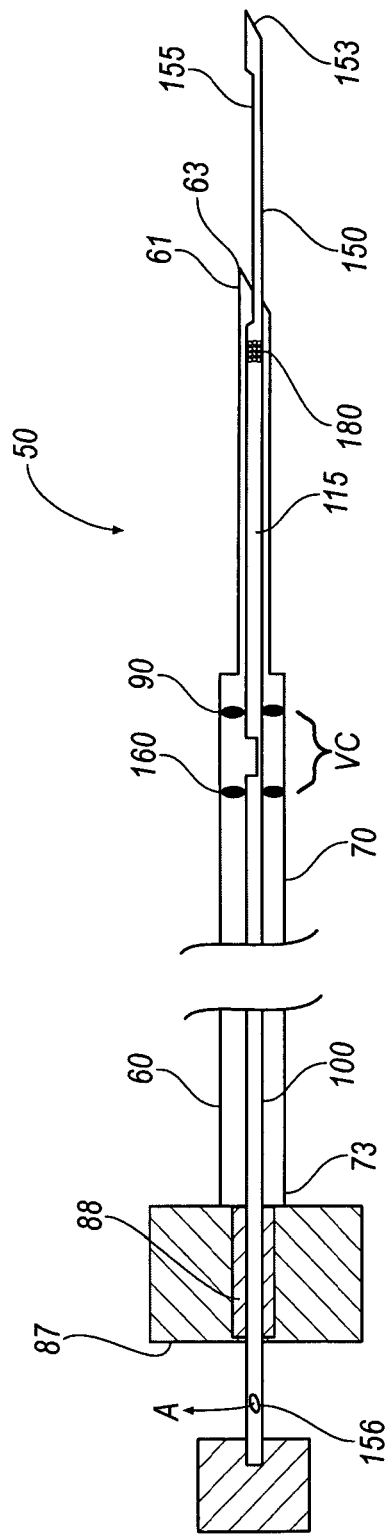
Figure 10:
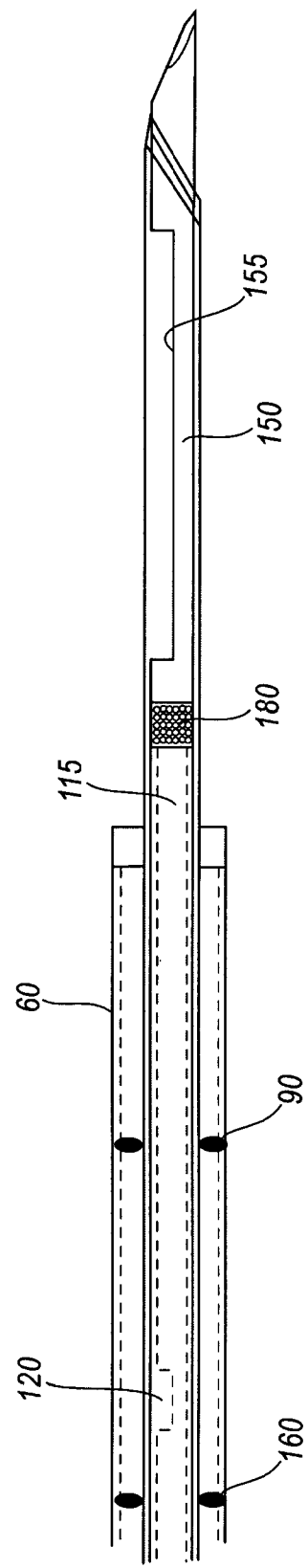
FIG. 10 is an enlarged side elevational view of the distal end of the needle set of FIG. 5.

As the device is cocked, the inner member 100 is pulled towards the operator, which exposes the vent aperture 156 beyond the proximal end 87 of the hub 80 of the outer cannula 60, as shown in FIG. 8. Referring to FIG. 9B, the inner member 100 is pushed forward to expose the cavity 155 to tissue, the vacuum chamber VC is collapsed, as indicated by the closer proximity between the cannula seal member 160 and the seal member 90. Accordingly, air A is vented out through the vent aperture 156 along the direction of arrow A. The vent aperture 156 is designed to prevent pushing air out though the cavity 155. Firing the device causes the outer member 60 to move distally, which expands the vacuum chamber VC. Expanding the vacuum chamber VC creates a vacuum in the inner lumen 115, which is communicated to the cavity 155 as the vent aperture 156 is sealed within vent seal 88 disposed within the hub lumen 85. The vacuum generated in the extended position serves to bias the tissue toward the sampling cavity 155 and hold the tissue in place while the suspect tissue is severed. Therefore, vacuum is applied to the tissue in cavity 155 as the tip member 61 of the outer member 60 moves over the sampling portion 150 of the inner member 100. In contrast, when prior art devices are used, the outer member tends to push tissue away from the cavity, reducing the size of the sample or requiring multiple attempts to capture the sample. In the embodiments of the present invention, the vacuum created by the enlargement of the vacuum chamber actually captures and holds the tissue within the cavity 155 resulting in more reliable sampling and larger sample volumes.

The needle set may also include a metering mechanism for selectively allowing the exchange of air but not tissue between the cavity 155 and the inner lumen 115. As shown more clearly in FIG. 10, in one particular embodiment, the metering mechanism includes a filter member 180 fitted within the inner lumen 115 or disposed between the inner lumen 115 and the sampling portion 150. Any suitable material may be employed for the filter member 180. However, the selected material should, but not necessarily, have a pore size that allows the exchange of air but is too small for body tissue.

An alternative embodiment of the metering mechanism includes the inner member 100' shown in FIGS. 11-13. The distal tip member 151' of sampling portion 150' includes tissue piercing tip 153' and a solid insert 158. As illustrated by FIGS. 12-13, solid insert 158 has an outer diameter OD that is less than the inner diameter ID of the inner lumen 115' so that air may pass around the insert 158 when the insert is disposed within the inner lumen 115'. As shown, the insert 158 is substantially centered within the inner lumen 115'. In alternate embodiments, based on design requirements, the insert 158 may be shifted to a particular side or portion of the inner lumen 115' thereby modifying the air flow within the inner lumen 115'. The insert 158 and the inner lumen 115' should be, but not necessarily, dimensioned so that the space between them allows air to pass but not tissue.

Figure 14:
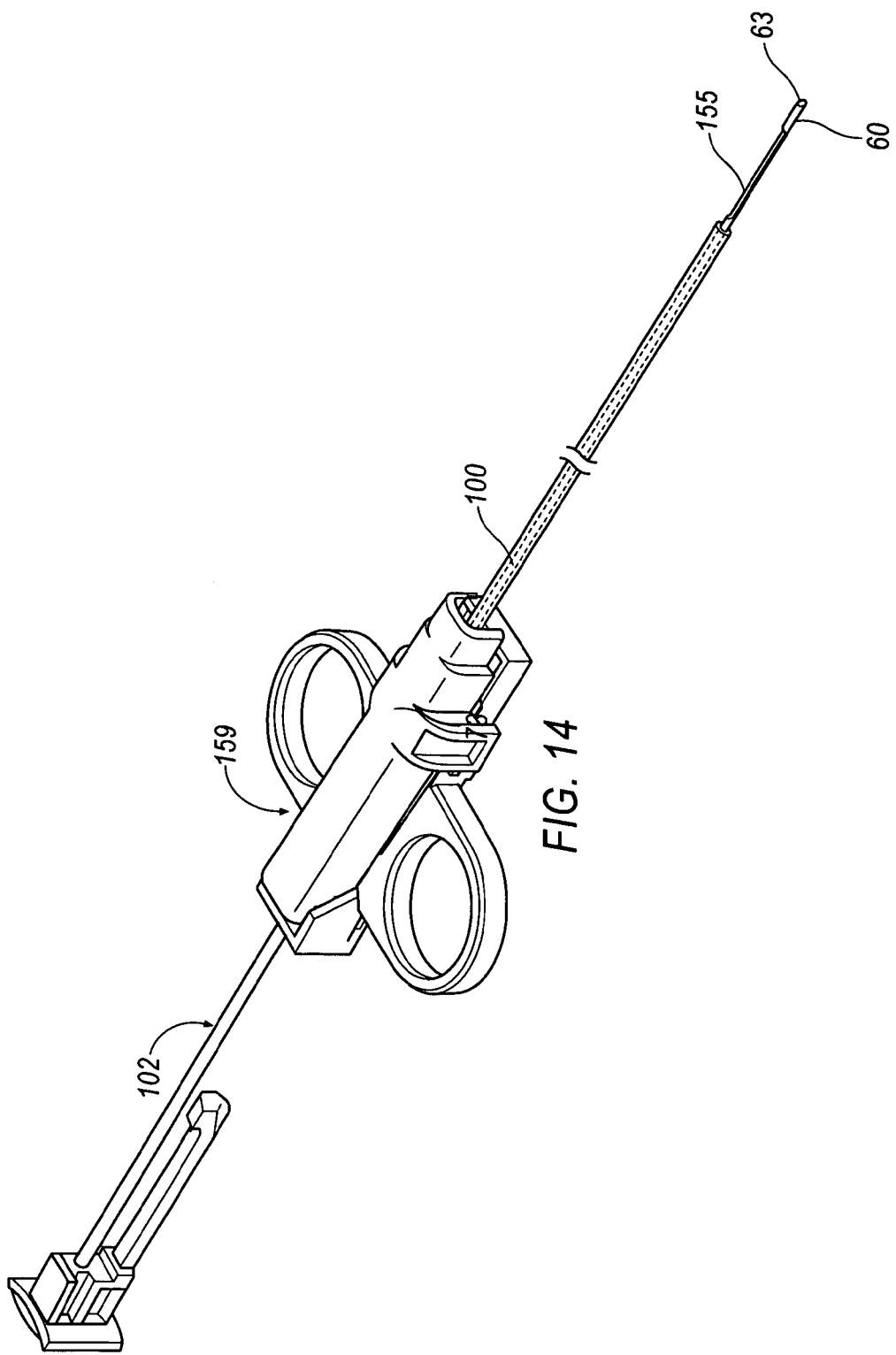
FIG. 14 is a perspective view of the needle set of FIG. 5 having a firing mechanism.

The needle set embodiments herein may be operated via a biopsy device. For example, the needle set can be loaded into a double action biopsy device or incorporated into a single action biopsy device. FIG. 14 illustrates a needle set including an advancing mechanism 159, operatively engaged to the second end 73 of the cylinder 70 and the proximal end 102 of the inner member 100. The advancing mechanism 159 is operable to move the outer member 60 relative to the inner member 100 from the second position to the first position to trap tissue from the biopsy site in the sampling cavity 155.

The embodiments of the inner member 100 described herein may be constructed according to the steps depicted in FIGS. 15-18. As shown in FIG. 15, insert 158 may be attached to a connecting element 158a and a blank 151". As shown in FIG. 16, insert 158 is positioned within the lumen 115' of the cannula 110', with the cannula 110' friction fitted to the connecting element 158a. The connecting element 158a could be a ring or a pair of projections, for example. The sampling cavity 155' is then machined through a distal portion 101' of the cannula 110' and into the solid insert 158 to achieve the configuration shown in FIGS. 17A-17B. The inner member 100 may be inserted into the cylinder lumen 75 of the outer member 60 (as shown in FIG. 8). A tissue piercing tip can be formed at any point in the process, using any suitable methods, such as by machining the blank 151".

Figure 18A:
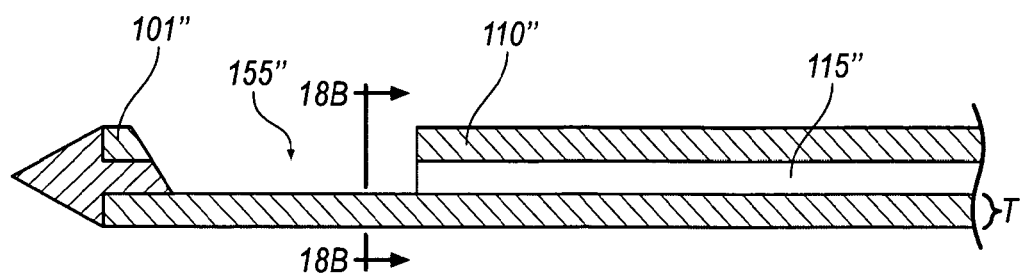
FIGS. 18A-18B illustrate a cross-sectional and end-view of a portion of the inner member of FIG. 7.
Figure 18B:
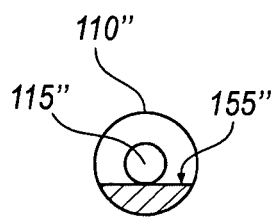

FIGS. 18A-18B illustrate an embodiment of an inner cannula 110" for use with the needle set described herein. The inner cannula 110" is formed having a thick exterior wall "T" whereby the diameter of the inner lumen 115" is smaller in comparison to thin walled inner cannula 110'. The distal end 101" of the inner cannula 110" is disposed with a tissue piercing tip through methods known to those skilled in the art. A sampling cavity 155" is formed in the distal portion of the inner cannula 110" proximate the tissue piercing tip. The inner cannula 110" is placed in communication with a vacuum source and a vacuum is delivered through the inner lumen 115" to the sampling cavity 155". The vacuum causes tissue at the biopsy site to be drawn into the sampling cavity 155" for excision during a biopsy procedure. FIG. 18B generally illustrates a cross-sectional end-view of the inner cannula 110" after the sampling cavity 155" has been formed. A portion of the exterior wall of the inner cannula 110" is removed to expose at least a portion of the inner lumen 115".

Figure 18C:
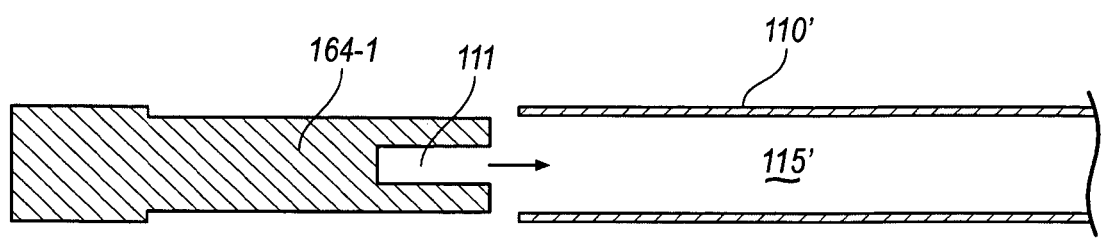
FIGS. 18C-18E illustrate sectional views of an embodiment of a vacuum bed formed in an inner cannula from a trocar blank.
Figure 18D:
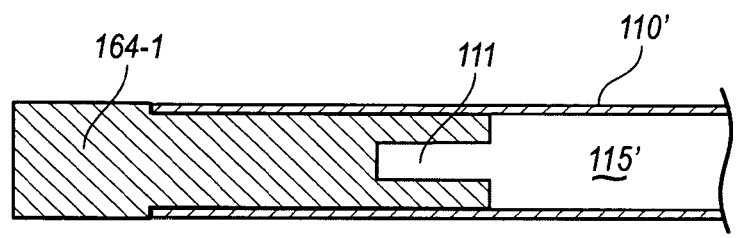
Figure 18E:
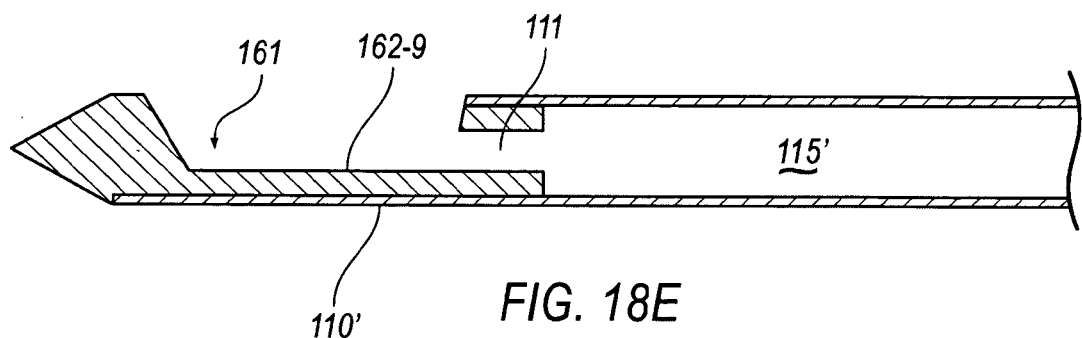

FIGS. 18C-18E illustrate a conventional thin walled inner cannula 110' wherein a vacuum bed 162-9 is formed by first inserting a trocar blank 164-1 into the inner lumen 115' at the distal end of the cannula 110'. The trocar blank 164-1 includes a notch 111 at its proximal end which is formed into a vacuum port when the sampling cavity 161 is formed in the inner cannula 110'. The inner cannula 110' is placed in communication with a vacuum source whereby a vacuum is delivered to the inner lumen 115' to the sampling cavity 161. The vacuum draws tissue into the sampling cavity 161 for excision during a biopsy procedure.

FIGS. 19-24 illustrate alternative embodiments wherein the distal portion 101' of the inner cannula 110' is configured as a vacuum bed (162-1 through 162-8). The vacuum beds (162-1 through 162-8) are configured to provide a uniform vacuum throughout the sampling cavity 161 in order to acquire more uniform and larger core samples. Additionally, the vacuum bed (162-1 through 162-8) operates to provide rigidity to the bottom of the inner cannula 110' which also allows for a deeper sampling cavity 161 to be formed.

Figure 19A:
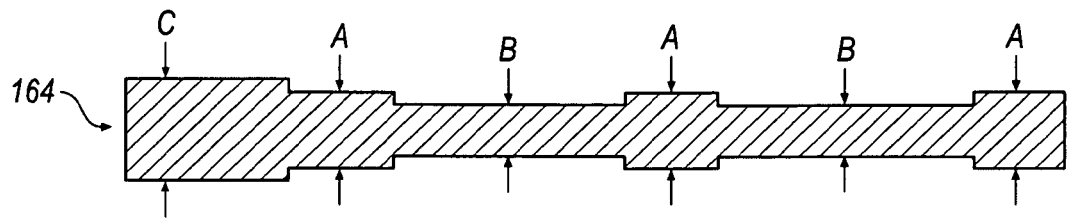
FIGS. 19A-19E illustrate an embodiment of a vacuum bed for use with embodiments of biopsy devices disclosed herein.
Figure 19B:
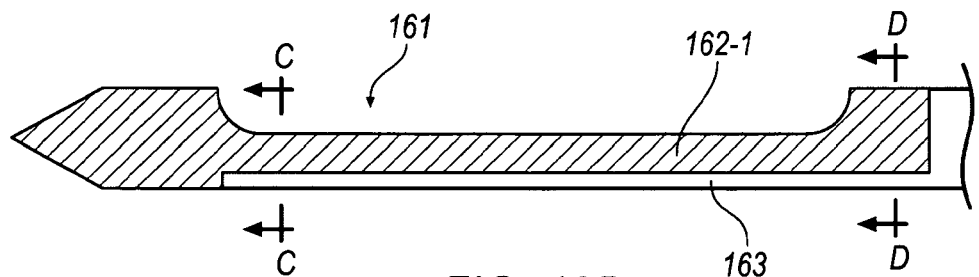
Figure 19C:
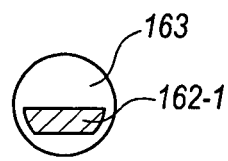
Figure 19D:
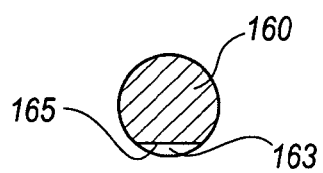
Figure 19E:
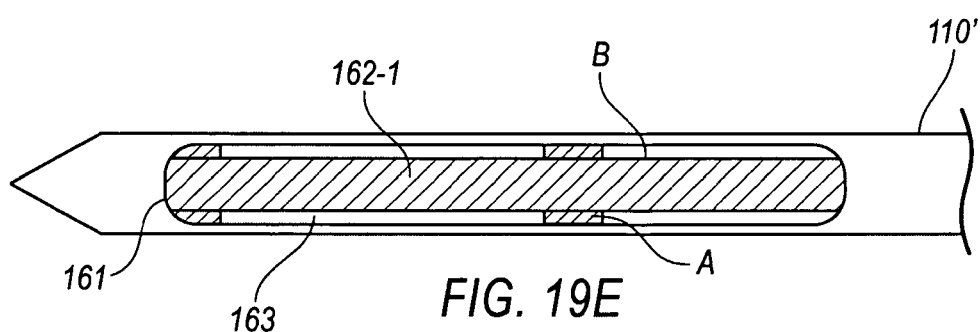

FIGS. 19A-19E illustrate a method of configuring a vacuum bed 162-1. It is appreciated that the method illustrated is merely exemplary as other methods for configuring the vacuum beds 162-1 through 162-8 are contemplated. FIG. 19A illustrates a trocar blank 164 used to form the vacuum bed 162-1. The trocar blank 164 is pressed into the distal portion 101' of the inner cannula 110'. The "A" dimension is sized to be a press-fit into the inner cannula 110' whereby it is retained by friction between itself and the lumen of the inner cannula 110'. In addition, the "A" dimension has a flat 165 to allow for vacuum travel beneath and along the sides of the vacuum bed 162-1. The "B" dimension is sized smaller than the inner diameter of the inner cannula 110'. Once pressed into the inner cannula 110', the trocar blank 164 and sampling cavity 161 are ground to form the vacuum bed 162-1 such as by machining. The trocar blank 164 then serves as the trocar tip and the vacuum bed 162-1 as illustrated in FIG. 19B. FIGS. 19C and 19D illustrate a vacuum channel 163 as being formed beneath and at the sides of the vacuum bed 162-1. In this fashion, the vacuum that is generated in the inner cannula 110' is uniformly distributed throughout the sampling cavity. FIG. 19E illustrates a top view of the vacuum bed 162-1 after the machining process is completed.

Figure 20A:
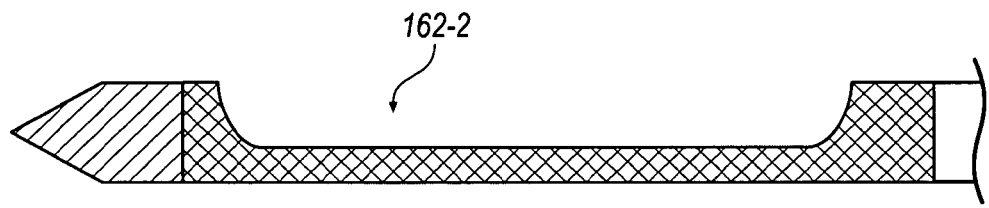
FIG. 20A illustrates a vacuum bed formed of a sintered or porous material blank.
Figure 20B:
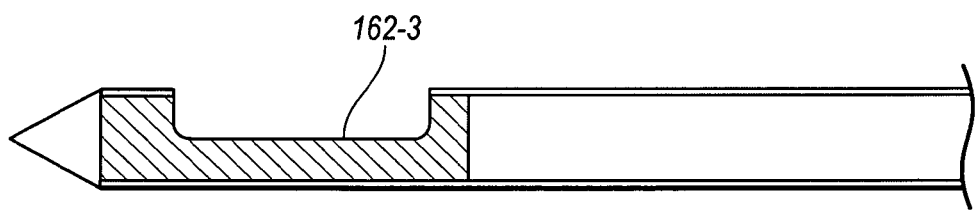
FIG. 20B illustrates a vacuum bed formed of a threaded material blank.
Figure 20C:
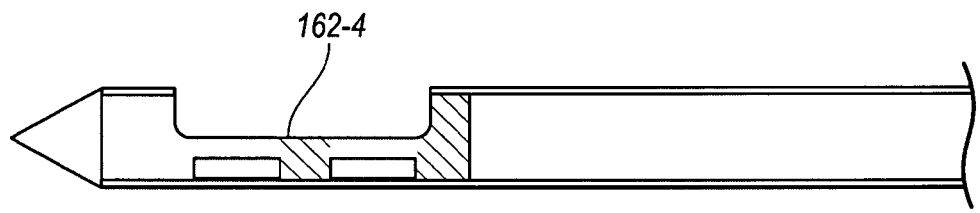
FIG. 20C illustrates a vacuum bed formed of a contoured material blank including threaded portions.

FIG. 20A illustrates a vacuum bed 162-2 formed with a sintered/porous material. The sintered/porous blank is press-it into the inner cannula 110' and machined as described above to form the vacuum bed 162-2. The pores in the sintered material allow vacuum to be pulled through the vacuum bed 162-2 and inner cannula 110', thereby pulling tissue into the sampling cavity 161. FIG. 20B illustrates a vacuum bed 162-3 configured from a threaded blank material and FIG. 20C illustrates a vacuum bed 162-4 configured from a contoured and partially threaded blank material. The threads in the blank material provide paths through which vacuum air can travel to the sampling aperture 161. Each of the vacuum beds (162-3 and 162-4) can be constructed in the manner described above or other method known to those skilled in the art.

Figure 21A:
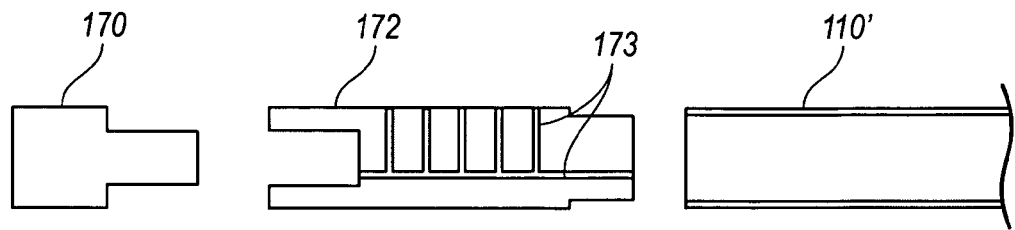
FIGS. 21A-21C illustrate a vacuum bed formed of a material blank assembly having pre-drilled vacuum passages.
Figure 21B:
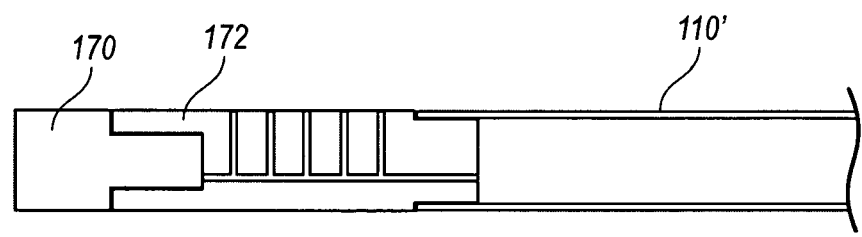
Figure 21C:
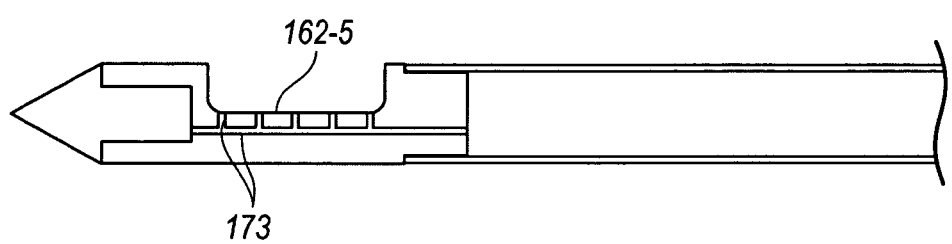

FIGS. 21A-21C illustrate a blank material subassembly used to form a vacuum bed 162-5 which contains pre-drilled vacuum passages 173. A trocar blank 170 and a chamber blank 172 are both machined from stock material. The trocar blank 170 is pressed into the chamber blank 172 as illustrated in FIG. 21B. The subassembled trocar blank 170 and chamber blank 172 are then pressed into the distal end 101' of the inner cannula 110' where it is retained by friction. Also, the joints between the subassembled components could be strengthened by laser welding the perimeter of each joint. Final construction consists of grinding the trocar blank 170 and chamber blank 172 to form a sharpened tip and vacuum bed 162-5, respectively, as illustrated in FIG. 21C. The vacuum is applied through the inner cannula 110' and travels through the drilled vacuum passages 173 to create a uniformly distributed vacuum at the sampling cavity 161.

Figure 22A:
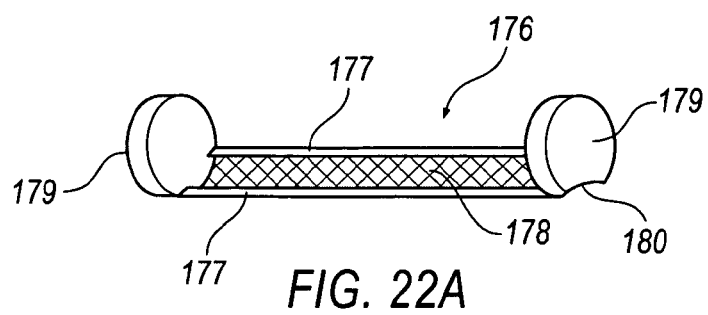
FIGS. 22A and 22B illustrate a vacuum bed formed from a framed mesh filter.
Figure 22B:
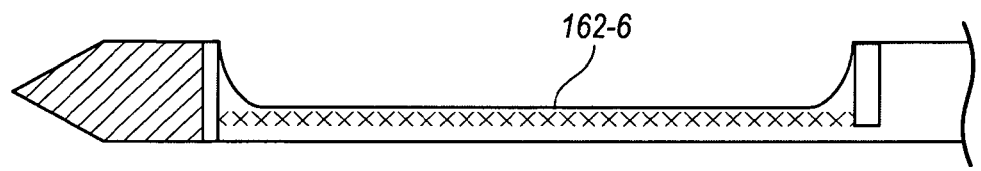

FIGS. 22A and 22B illustrate a vacuum bed 162-6 formed from a framed mesh filter 176. The framed mesh filter 176 includes substantially parallel and rigid elongated frame bars 177 which operate to support the mesh filter material 178 between disc-like end portions 179. The framed mesh filter 176 is fixed in the inner cannula 110' by friction fit between the disc-like end portions 179 and the sampling cavity 161 (See FIG. 22B. Alternatively, the framed mesh filter 176 may be spot welded at appropriate points to the inner cannula 110'. The disc-like end portion 179 adjacent the proximal end of the sampling cavity 161 preferably includes a vacuum channel 180 which allows for vacuum in the inner cannula 110' to travel beneath the framed mesh filter 176. The vacuum channel 180 and framed mesh filter 176 allow for delivery of vacuum to the sampling cavity 161 while preventing the extrusion of tissue down the inner cannula 110'.

Figure 23A:
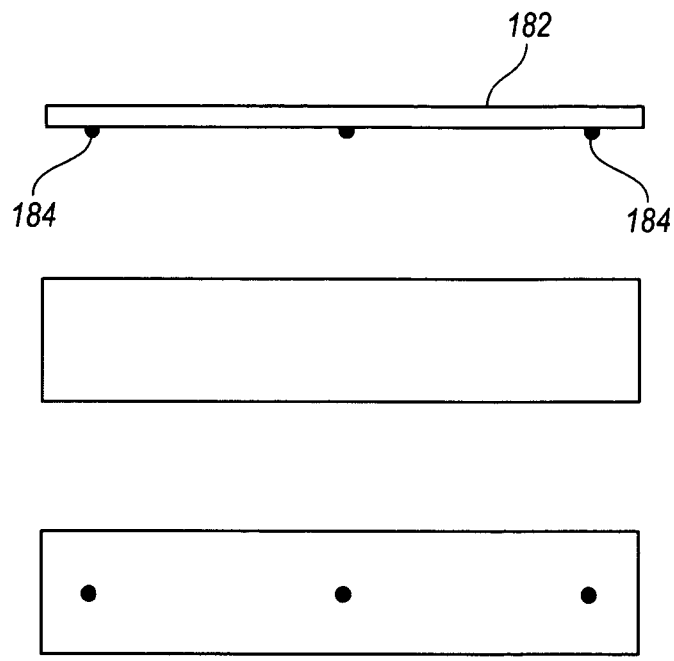
FIGS. 23A-23C illustrate a vacuum bed formed of a plate material.
Figure 23B:
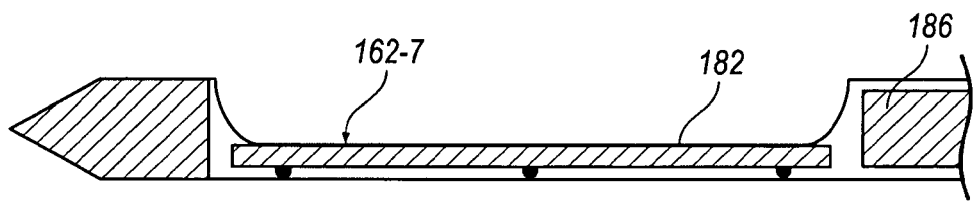
Figure 23C:
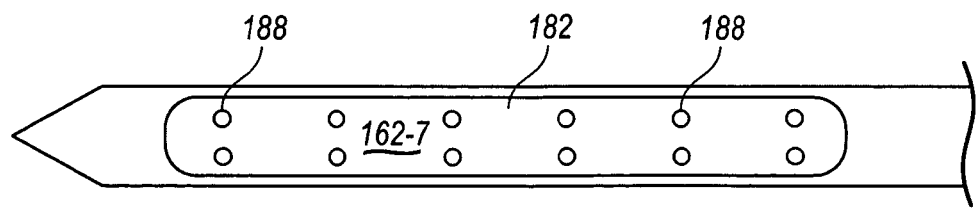
Figure 23D:
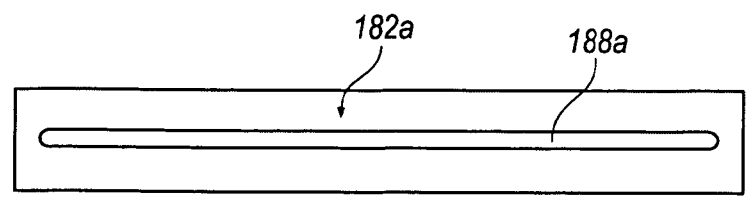
FIGS. 23D-23H illustrate alternative embodiments of the vacuum bed.
Figure 23E:
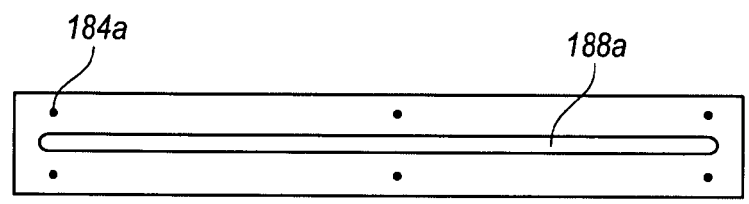
Figure 23F:
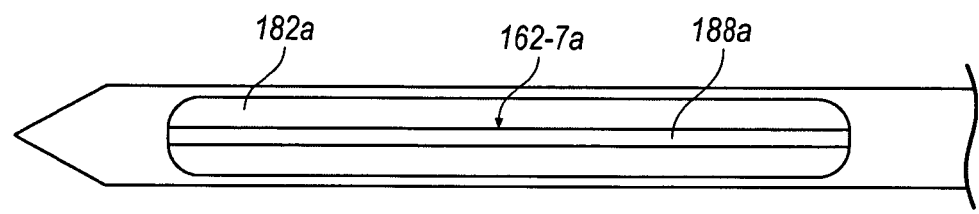
Figure 23G:
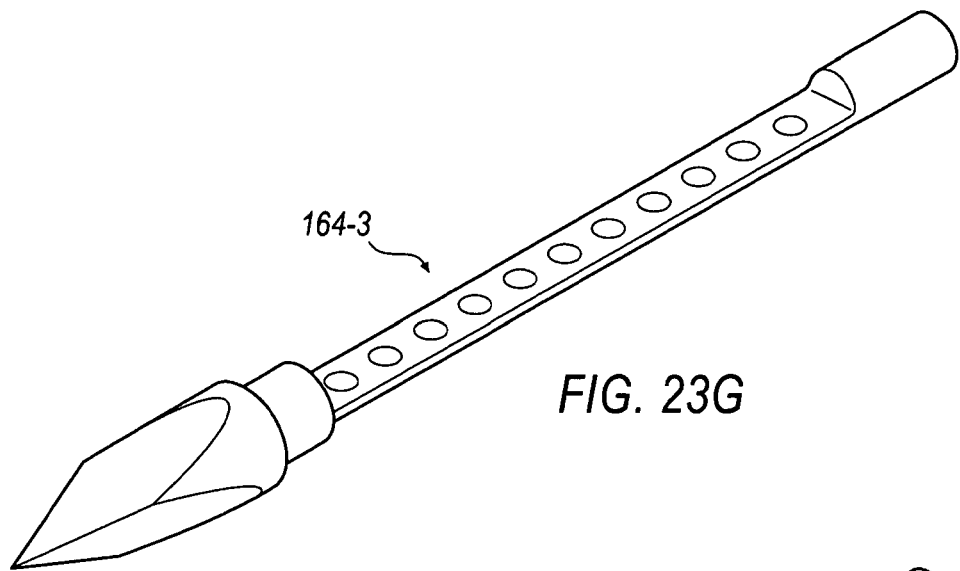
Figure 23H:
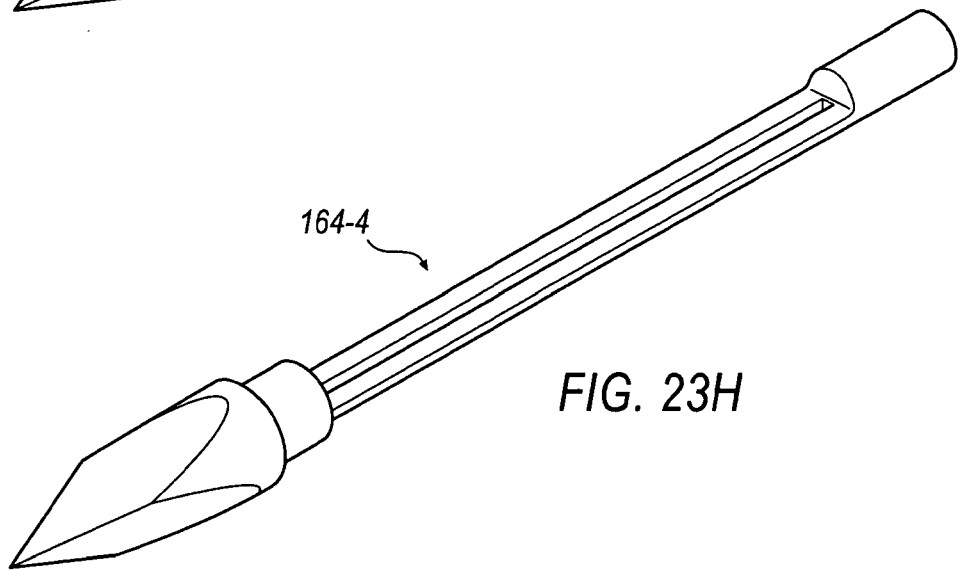

FIGS. 23A through 23E illustrate an alternative method of forming a vacuum bed 162-7 through the use of an elongated plate 182 having a plurality of weld points 184 disposed on a bottom surface thereof. In this embodiment, the sampling cavity 161 and the sharpened trocar tip will be ground on the inner cannula 110' prior to spot welding the plate 182 within the sampling cavity 161 to form the vacuum bed 162-7. A rod or plug 186 may be inserted into the inner cannula 110' to prevent the extrusion of tissue down the inner cannula 110' (See FIG. 23B). As best illustrated in FIG. 23C, the vacuum bed 162-7 may include a plurality of vacuum grooves or holes 188 to aide in pulling tissue into the sampling cavity 161 via the vacuum. FIGS. 23D-23F illustrate an embodiment of a vacuum bed 162-7a formed using the plate 182a that includes a plurality of weld points 184a disposed on the bottom surface thereof (See FIG. 23E) and at least one elongated hole or slit 188a formed along its longitudinal axis. The elongated slit 188a permits a vacuum to be distributed substantially the entire length of the elongated plate 182a. In addition to the forming the vacuum beds (162-7, 162-7a) using the respective elongated plates (182, 182a), stylaric inserts (164-3, 164-4) may be disposed in the inner lumen 115' through the open distal end of the inner cannula 110' (See FIGS. 23G-23H). The stylaric inserts (164-3, 164-4) are one piece structures that include a tissue piercing tip and the vacuum bed. The stylaric inserts (164-3, 164-4) are configured to be press fitted into the distal end of the inner cannula 110' and may be secured using an adhesive or by other methods known to those skilled in the art. It is appreciated that the stylaric inserts (164-3, 164-4) illustrated in FIGS. 23G-23H are merely exemplary of various embodiments which would be suitable for use with biopsy devices described herein and are not intended to be limiting with respect to other configurations.

Figure 24A:
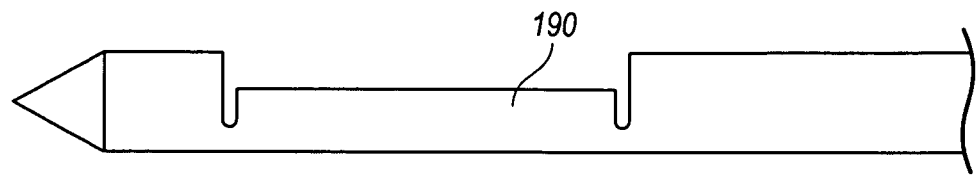
FIGS. 24A-24D illustrate a vacuum bed configured from bendable tabs formed on the cannula.
Figure 24B:
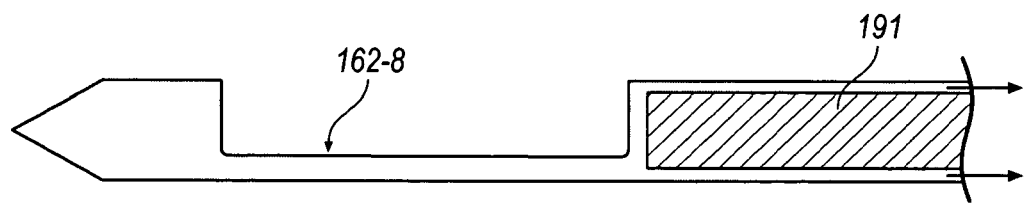
Figure 24C:
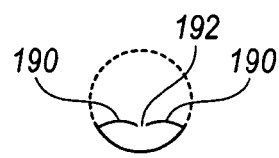
Figure 24D:
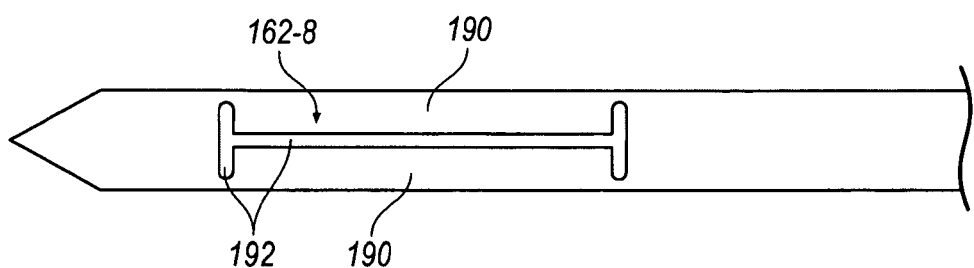

FIGS. 24A through 24D illustrate an embodiment of a vacuum bed 162-8 configured from cut and bend tabs 190 formed in the inner cannula 110'. First the tabs 190 are cut into the inner cannula 110' and then are bent to form the vacuum bed 162-8. As best illustrated in FIG. 24B, a rod 191 may be placed inside the inner cannula 110' to prevent extrusion of tissue therethrough but allows for vacuum to be delivered to the sampling cavity 161. FIG. 23C illustrates a transverse view of the vacuum bed 162-8 wherein tabs 190 are shown bent inward to vacuum slits 192 which allow vacuum to flow through the sampling cavity 161. FIG. 24D illustrates a top view of the vacuum bed 162-8 providing a detailed view of the vacuum slits 192.

Figure 25:
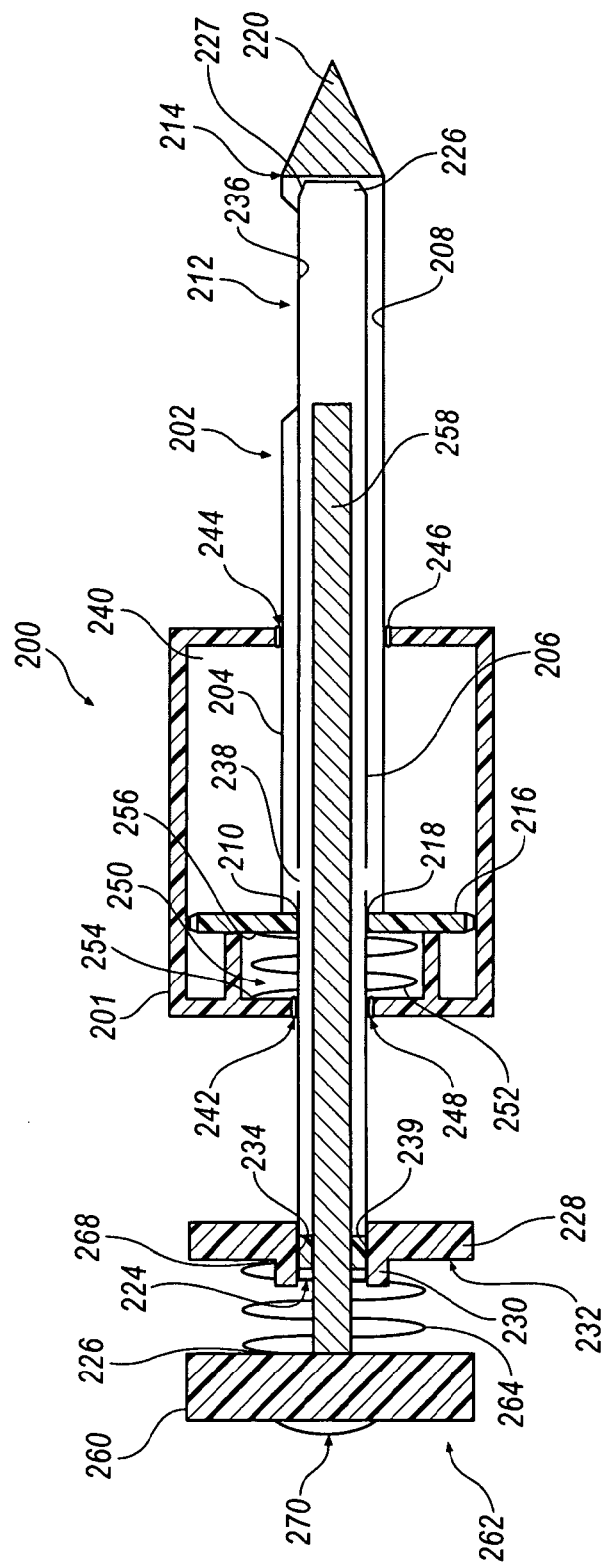
FIG. 25 is a cross-sectional view of an embodiment of a double-action biopsy device.

FIG. 25 illustrates an embodiment of a double action vacuum assisted biopsy device 200. The biopsy device 200 provides a handpiece 201 that includes a cutting element 202 having an outer cannula 204 and an inner cannula 206. The outer cannula 204 includes an inner lumen 208, an open proximal end 210, a tissue receiving aperture 212 disposed proximate a closed distal end 214, and a cylinder seal 216 having a central aperture 218 disposed at the open proximal end 210 thereof. Preferably, the outer cannula 204 includes a tissue piercing tip 220 that forms the closed distal end 214. The cylinder seal 216 is fixed to the open proximal end 210 such that the central aperture 218 is preferably concentrically positioned relative to the open proximal end 210 wherein the diameter of the central aperture 218 is smaller than the diameter of the open proximal end 210.

The cutting element 202 also includes an inner cannula 206 slidably disposed within the outer cannula 204. The inner cannula 206 is formed with an open proximal end 224 and an open distal end 226. The open proximal end 224 is disposed with a push plate 228 having a spring collar 230 formed on a proximal side 232 thereof. The spring collar 230 surrounds an opening 234 formed central to push plate 228. The opening 234 has a diameter dimensioned such that the open proximal end 224 of the inner cannula 206 can be frictionally fixed therein and/or fixed therein with an adhesive suitable for such purpose.

The open distal end 226 is preferably formed with a razor sharpened beveled edge 227 that enhances the tissue cutting ability of the inner cannula 206. The inner cannula 206 also includes an inner lumen 236 and at least one vacuum inlet 238 in fluid communication with the inner lumen 236 that is formed through the sidewall of the inner cannula 206. An outer diameter of the inner cannula 206 is dimensioned such that it can be slidably passed through the central aperture 218 of the cylinder seal 216 while maintaining a fluid seal in relation thereto. The inner lumen 236 also includes a vacuum seal 239 disposed proximate the open proximal end 224. The vacuum seal 239 is selectively engaged and configured to assist in maintaining a vacuum within the inner lumen 236 in a manner to be described hereinafter.

A vacuum chamber 240 is disposed about a portion of the cutting element 202 that includes the open proximal end 210 of the outer cannula 204 and cylinder seal 216, and the at least one vacuum inlet 238 of the inner cannula 206. The vacuum chamber 240 includes an open proximal end 242 and an open distal end 244. The open proximal end 242 of the vacuum chamber 240 has an inner diameter dimensioned to allow the inner cannula 206 to slidably pass therethrough. Preferably, the open proximal end includes a fluid sealing member 246 such as an O-ring that is configured to maintained a fluid seal between the inner cannula 206 and the open proximal end 242 of the vacuum chamber 240. The open distal end 244 of the vacuum chamber 240 has an inner diameter that is dimensioned to allow the outer cannula 204 to slidably pass therethrough. Preferably, a fluid sealing member 248 is disposed at the open distal end 244 of the vacuum chamber 240 that is configured to maintain a fluid seal between the open distal end 244 of the vacuum chamber 240 and the outer cannula 204.

The vacuum chamber 240 includes an internal spring housing 250 formed about the open proximal end 242 and extending axially toward the open distal end 244. The internal spring housing 250 is preferably formed concentric to the open proximal end 242 and is disposed with a first firing spring 252. The first firing spring 252 includes a proximal end 254, a distal end 256, and an inner diameter that is dimensioned to allow the inner cannula 206 to pass freely therethrough. The first firing spring 252 is disposed within the internal spring housing 250 such that the proximal end 254 contacts the open proximal end 242 of the vacuum chamber 240 and the distal end 256 contacts the cylinder seal 216.

As best illustrated in FIG. 27, the vacuum chamber 240 may also include a one way flow valve 257. The one way flow valve 257 is in communication with a fluid reservoir 259 filled with an absorbent material 261. The fluid reservoir 259 is configured to receive and retain a volume of fluid from the vacuum chamber 240 that may accumulate therein during the biopsy procedure. The absorbent material 261 cooperates with the fluid reservoir 259 to receive and retain the volume of fluid.

Referring again to FIG. 26, a tissue stop 258 is provided and configured to be slidably received within the inner lumen 236 of the inner cannula 206 through the vacuum seal 239 disposed at the open proximal end 224 thereof. In one embodiment, the tissue stop 258 extends the entire length of the inner cannula 206 from the open proximal end 224 to the open distal end 226 thereof. The tissue stop 258 includes a knob portion 260 disposed at a proximal end 262 thereof which may be used for adjusting the position of the tissue stop 258 within the inner cannula 206.

A second firing spring 264 is disposed between the knob portion 260 of the tissue stop 258 and the push plate 228 of the inner cannula 206. A proximal end 266 of the second firing spring 264 engages the knob portion 260 and a distal end 268 engages the push plate 228 about the spring collar 230. Preferably, the second firing spring 264 is fixed to at least one of the knob portion 260 or push plate 228 to enhance the overall stability of the biopsy device 200.

A trigger mechanism 270 is provided and configured to cause the first firing spring 252 to advance the outer cannula 204 distally outwardly such that the closed proximal end 220 of the outer cannula 204 penetrates into the biopsy site. Shortly therafter, the second firing spring 264 causes the inner cannula 206 to move distally outwardly whereby a tissue sample drawn into the tissue receiving aperture 212 is severed and retained in the inner lumen 236 of the inner cannula 206.

Figure 26A:
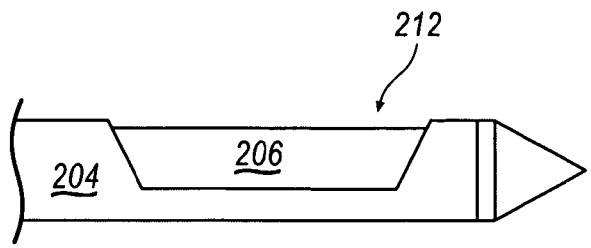
FIGS. 26A-26E are cross-sectional views of a second embodiment of a double-action biopsy device.
Figure 26B:
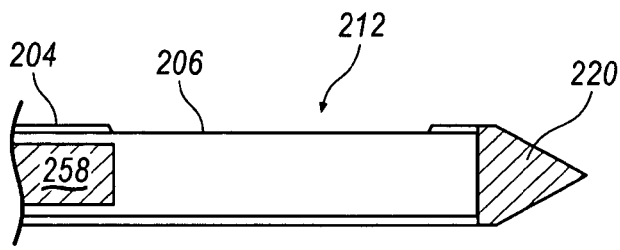

Referring now to FIGS. 25 and 26A through 26E, before performing a biopsy procedure with the biopsy device 200, the device 200 is cocked by holding the handpiece and compressing the first and second firing springs (252, 264) until they are cocked (See FIGS. 25-26B). Thereafter, the biopsy device 200 is positioned for penetration into the biopsy site.

Figure 26C:
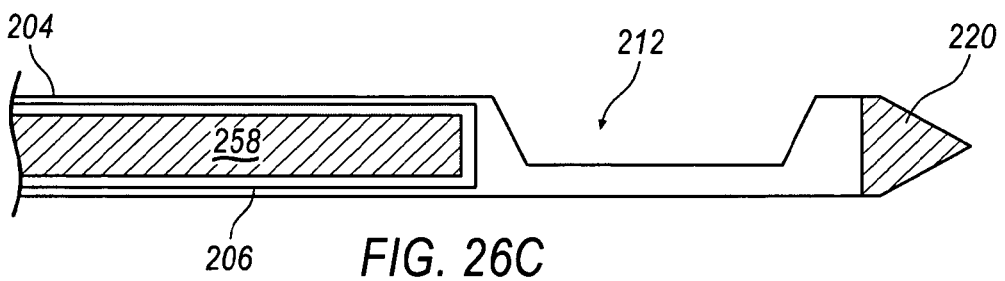
Figure 26D:
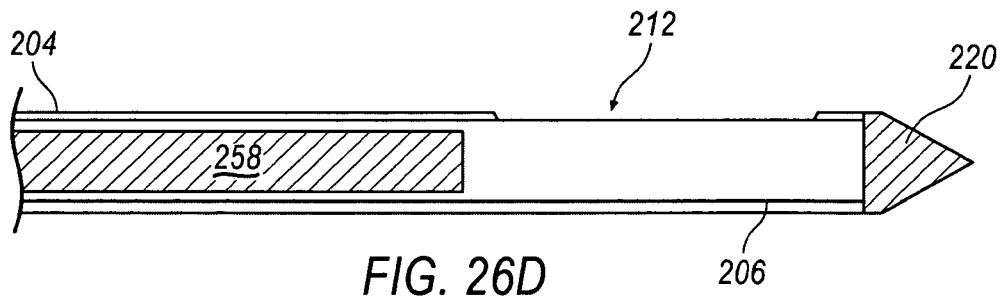

Next at FIG. 26C, the trigger mechanism 270 is actuated causing the release of the first 252 firing spring. When the outer cannula 204 is advance distally outwardly by the first firing spring 252 into the biopsy site, the cylinder seal 216 within the vacuum chamber 240 is advanced forward such that it passes the at least one vacuum inlet 238 formed in the wall of the inner cannula 206. Once the cylinder seal 216 passes the at least one vacuum inlet 238, a vacuum is generated in the vacuum chamber 240 that is delivered to the tissue receiving aperture 212 via the inner lumen 236 of the inner cannula 206. The vacuum also causes the one-way valve 257 (See FIG. 27) to close such that the vacuum is maintained within vacuum chamber 240. Further, the vacuum seal 239 is caused to engaged the tissue stop 258 such that the vacuum can be maintained at the inner lumen 236. The vacuum generated by the vacuum chamber 240 operates to cause tissue at the biopsy site to be drawn into the tissue receiving aperture 212 thus improving the chances that a sufficent tissue sample will be obtained Referring now to FIG. 26D, a short predetermined period after the outer cannula 204 has been fired, the inner cannula 206 is advanced distally outwardly by the second firing spring 264. The sharpened beveled edge 227 of the inner cannula 206 severs the tissue drawn into the tissue receiving aperture 212 and the tissue sample is held within the inner lumen 236 of the inner cannula 206 proximate the open distal end 226 thereof by the tissue stop 258. To further enhance to cutting ability of the inner cannula 206, it may be configured to rotate as it is advanced distally outwardly creating a slicing and shearing action for severing the tissue.

Figure 26E:
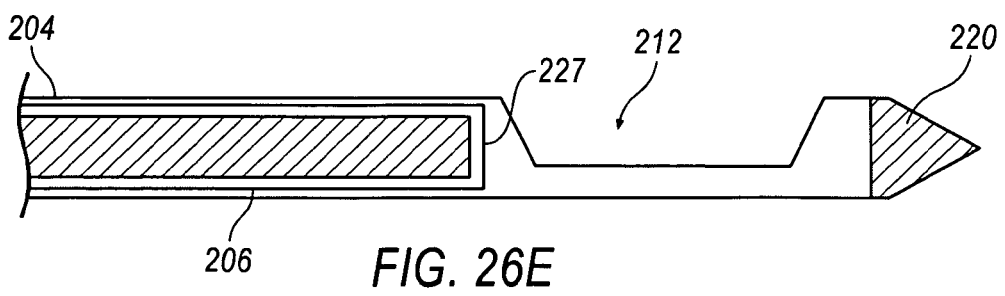

Referring now to FIG. 26E, after removing the biopsy device 200 from the biopsy site, the tissue sample can be retrieved from the tissue receiving aperture 212 of the outer cannula 204 by retracting the inner cannula 206 whereby the tissue sample is exposed for removal. The biopsy device 200 is thereafter cocked causing the vacuum seal 239 and the one-way valve 257 to open whereby the vacuum is released and any fluid built up within the vacuum chamber 240 is allowed to flow into the fluid reservoir 259 (See FIG. 27).

As best illustrated in FIG. 28, an embodiment of the biopsy device 200 may be configured to cooperate with the fluid reservoir 259 being disposed in-line between the vacuum chamber 240 and a vacuum source 280. The vacuum source 280 may be any fluid source capable of providing a vacuum to the biopsy device 200, for example, a vacuum generating machine or a $CO_2$ cartridge. Preferably, the vacuum source 280 communicates with the vacuum chamber 240 through tubing 282 and a vacuum port 284. In this embodiment, the open proximal end 210 of the outer cannula 206 is disposed with a flange 286 that seats over the internal spring housing 250 when the biopsy device 200 is cocked such that the first firing spring 252 is in mechanical communication therewith. Preferably, the actuation of the trigger mechanism 270 causes the first firing spring 252 to advance the outer cannula 204 distally outwardly and the vacuum source 280 to power on such that a vacuum is generated in the vacuum chamber 240. The generated vacuum is delivered to the inner cannula 206 via the at least one vacuum inlet 238. The vacuum causes tissue at the biopsy site to be drawn into the tissue receiving aperture 212 of the outer cannula 204. Thereafter, the second firing spring 264 causes the inner cannula 206 to be advanced distally outwardly whereby the tissue within the tissue receiving aperture 212 is severed. Fluid entering the vacuum chamber 240 is drawn through the vacuum port 284 and tubing 282 into the fluid reservoir 259. After the tissue sample has been obtained the vacuum source 280 is turned off and the tissue sample can be removed from the biopsy device 200 in the manner described above.

Figure 29A:
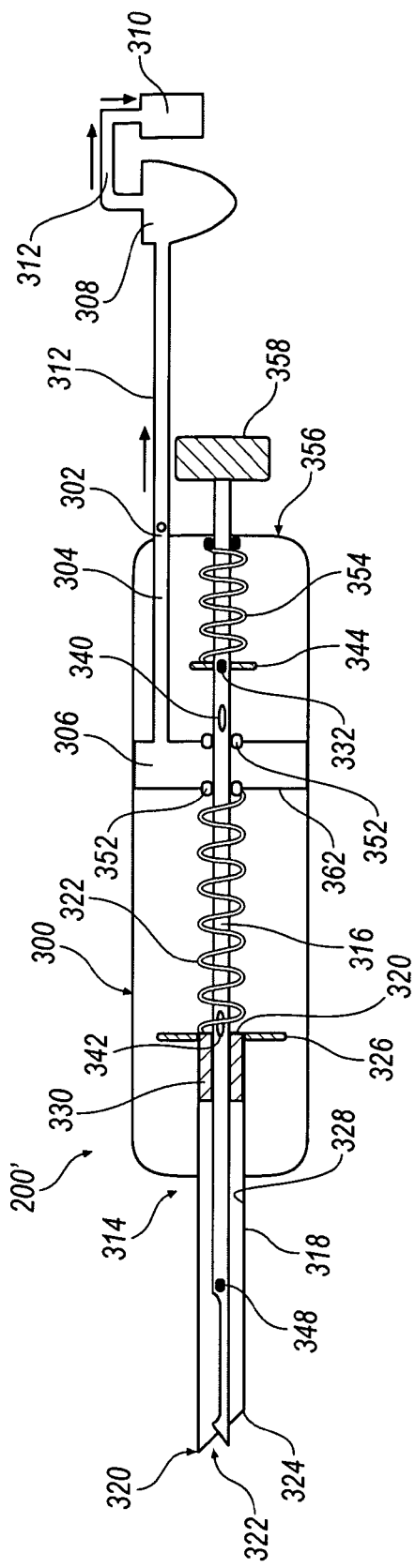
FIGS. 29A-29C are cross-sectional views of a third embodiment of a double-action biopsy device.

Another embodiment 200' of the biopsy device is configured to allow the inner cannula 206 to be fired prior to firing the outer cannula 204. In the embodiment FIGS. 29A through 29C, the handpiece 300 includes the vacuum port 302 in communication with a vacuum channel 304 that communicates with vacuum chamber 306. The vacuum port 302 also communicates with a fluid reservoir 308 and vacuum source 310 through tubing 312. The cutting element 314 includes an inner cannula 316 and an outer cannula 318 wherein a portion of the cutting element 314 is housed by the handpiece 300. The outer cannula 318 includes open proximal 320 and distal 322 ends wherein the open distal end 322 preferably includes a razor sharpened edge 324 and the open proximal end 320 includes a second spring flange 326 formed integral thereto. The inner lumen 328 of the outer cannula 318 includes a vent seal 330 disposed proximate the open proximal end 320 thereof.

Figure 29B:
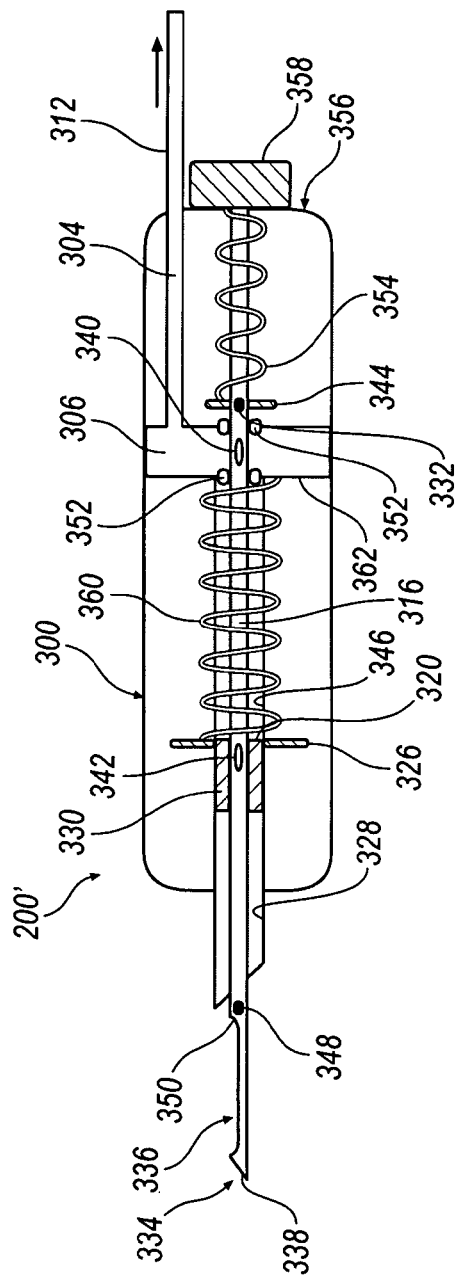
Figure 29C:
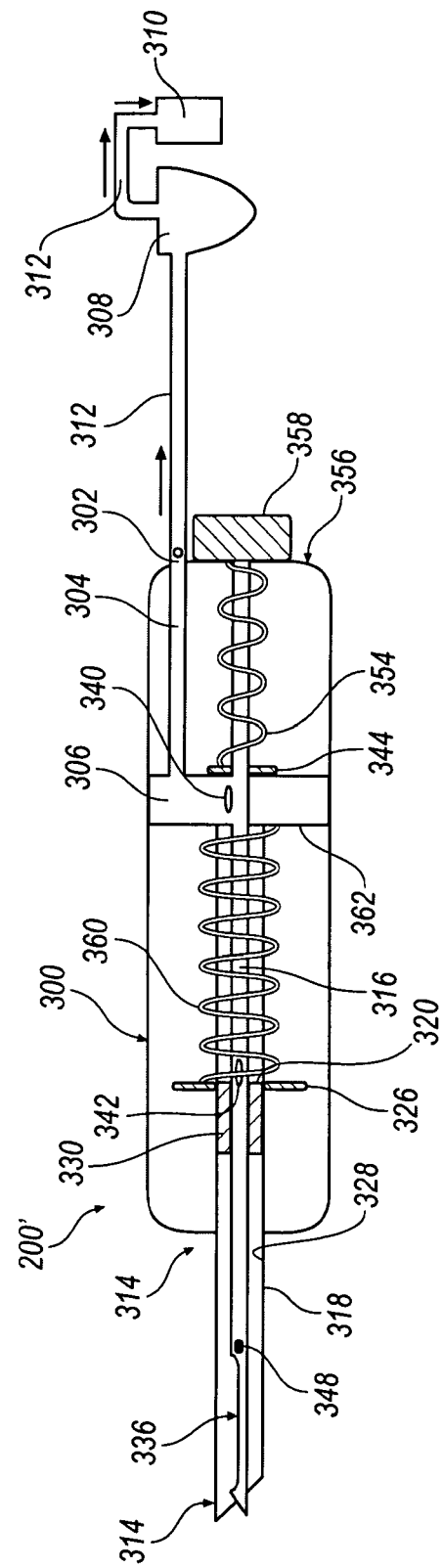

The inner cannula 316 includes a closed proximal end 332 and a closed distal end 334 wherein the closed distal end 334 is disposed with a tissue receiving aperture 336 proximate thereto (See FIG. 29B). The closed distal end 334 is provided as a working end formed with a sharp tip 338 for penetrating through tissue into the biopsy site. The inner cannula 316 includes at least one vacuum inlet 340 formed proximate the closed proximal end 332 and at least one vent aperture 342 formed between its proximal 332 and distal 334 ends. The closed proximal end 332 includes a first spring flange 344 formed integral thereto. Preferably, the inner lumen 346 of the inner cannula 316 is disposed with a tissue stop 348 proximate a proximal end 350 of the tissue receiving aperture 336. The inner cannula 316 is configured with an outer diameter that allows it to be slidably received into the outer cannula 318 through the vent seal 330 while maintaining a fluid seal therewith. The inner cannula 316 passes through the vacuum chamber 306 along a longitudinal axis of the handpiece 300. The sidewalls of the vacuum chamber 306 include seal members 352, for example, O-rings at the location where the inner cannula 316 passes along the longitudinal axis. The inner cannula 316 has an outer diameter dimensioned to slidably pass through the seal members 352 while maintaining a fluid seal therebetween.

Referring now to FIG. 29B, the first firing spring 354 is disposed about the inner cannula 316 between the first spring flange 344 and the proximal end 356 of the handpiece 300. The first firing spring 354 operates to advance the inner cannula 316 distally outwardly into the biopsy site after the trigger mechanism 358 has been actuated. The second firing spring 360 is disposed about the inner cannula 316 between the second spring flange 326 and the distal sidewall 362 of the vacuum chamber 306. The second firing spring 360 causes the outer cannula 318 to be advanced distally outwardly after the inner cannula 316 has been fired (See FIG. 29C).

Upon actuating the trigger mechanism 358, the first firing spring 354 advances the inner cannula 316 distally outwardly such that the working end penetrates into the biopsy site and causes the at least one vent aperture 342 to become closed by the vent seal 330. Additionally, the at least one vacuum inlet 340 is advanced to a position within the vacuum chamber 306. The vacuum source 310 is powered on and a vacuum is generated in the vacuum chamber 306 which is delivered to the inner cannula 316 through the vacuum inlet 340. The vacuum source 310 may be turned on manually or automatically in response to the inner cannula 316 being fired. The vacuum causes tissue to be drawn into the tissue receiving aperture 336 of the inner cannula 316 and fluid from the biopsy site to be drawn into the fluid reservoir 308.

After the inner cannula 316 has been fired, the outer cannula 318 is advanced distally outwardly by the second firing spring 360 and the tissue drawn into the tissue receiving aperture 336 of the inner cannula 316 is severed and held in the inner lumen 346 of the inner cannula 316 proximate the tissue receiving aperture 336 by the tissue stop 348. The outer cannula 318 may be configured to rotate while being advanced distally outwardly thereby producing a slicing and shearing action for severing the tissue at the biopsy site. After the biopsy device 200' is removed, the tissue sample is removed by turning off the vacuum source 310 and retracting the outer cannula 318 such that the tissue sample is exposed.

FIGS. 30A-30D illustrate another embodiment 200" of a biopsy device having a cutting element mounted to a housing. With reference to FIG. 30A, the biopsy device 200" includes a housing 400 having a cutting element 402. The cutting element 402 includes an inner cannula 404 and an outer cannula 406. As best illustrated in FIG. 30B, the inner cannula 404 has a sharpened tip 405 formed at its distal end 414. A tissue receiving aperture 412 is formed proximal to the sharpened tip 405 and is configured for receiving tissue to be excised in the cutting process to be described below.

Still referring to FIG. 30B, the inner cannula 404 is slidably disposed within the outer cannula 406. Preferably, the outer cannula 406 includes a razor sharpened beveled edge 416 formed at its distal end 418 for enhancing its ability to cut tissue.

A vacuum chamber 408 is disposed proximate the proximal end 420 of the inner cannula 404. The vacuum chamber 408 operates to cause a vacuum to be generated in the inner cannula 404 whereby tissue to be excised is drawn into the tissue receiving aperture 412 such that the probability of obtaining an adequate sample is increased.

As illustrated in FIG. 30C, a trigger mechanism 410 is provided for causing the cutting element 402 to excise a tissue sample as will be described below. The trigger mechanism 410 includes a first trigger arm 422 which causes the firing of inner cannula 404 when actuated and a second trigger arm 424 which causes the firing of the vacuum chamber 408 and, thereafter, the firing of the outer cannula 406 during the biopsy procedure. A biopsy procedure using the present embodiment will be described with reference to FIGS. 30A-30D. FIG. 30A illustrates the biopsy device 200" wherein the inner cannula 404, outer cannula 406 and vacuum chamber 408 are retained in a cocked position by the first 422 and second 424 trigger arms of the trigger mechanism 410.

Referring to FIG. 30B, the trigger mechanism 410 is actuated to cause the first trigger arm 422 to allow the firing of the proximal end 414 of the inner cannula 404 into the biopsy site. Next, as best illustrated in FIG. 30C, the trigger mechanism 410 is actuated a second time to cause the second trigger arm 424 to allow the vacuum chamber 408 to be fired. Firing of the vacuum chamber 408 causes a vacuum to be generated in the inner cannula 404 whereby tissue at the biopsy site is drawn into the tissue receiving aperture 412. In addition to causing the vacuum to be generated in the inner cannula 404, as illustrated in FIG. 30D, the firing of the vacuum chamber 408 causes the outer cannula 406 to fired whereby the tissue drawn into the tissue receiving aperture 412 is severed. The tissue sample may be removed from the inner cannula 404 by pulling the outer cannula 406 back to the cocked position to expose the tissue sample.

In one embodiment 500, the biopsy device is moved from an uncocked position to a cocked position by squeezing the handle 510 of the biopsy device three consecutive times to sequentially return the vacuum hub 502, the inner cannula hub 504, and the outer cannula hub 506 to the cocked position via an actuating platform 508. The actuating platform 508 is spring loaded and slidably reciprocates between uncocked and cocked positions within the biopsy device. Squeezing the handle 510 of the biopsy device a first time causes the vacuum hub 502 to move from a uncocked position to a cocked position. A second squeeze causes the inner cannula hub 504 to move from a uncocked position to a cocked position and a third squeeze causes the outer cannula hub 506 to move from an uncocked position to a cocked position. The handle 510 of the biopsy device must be squeezed three times before any one core can be retrieved from the biopsy device after it has been severed.

The assemblies of this invention can be provided in any suitable shape and size and can be manufactured using any suitable materials. In one particular embodiment, the needle set is composed of surgical grade stainless steel. Other embodiments of the invention will be apparent to those skilled in the art from consideration of the specification and practice of the invention disclosed herein. It is intended that the specification, drawings and examples be considered as exemplary only, with the true scope and spirit of the invention being indicated by the following claims. It should be understood that the embodiments shown and described and all changes and modifications that come within the spirit of the invention are desired to be protected.

What is claimed is:

1. A tissue removal device, comprising:
    a tissue receiving cannula defining a tissue receiving opening near a distal end thereof and a tissue receiving cannula lumen in fluid communication with the tissue receiving opening formed in a sidewall of the tissue receiving cannula, the tissue receiving opening being configured to receive a tissue sample positioned adjacent the tissue receiving opening;
    a cutting cannula defining an open distal end, a vacuum inlet, and a cutting cannula lumen in fluid communication with the cutting cannula open distal end and the vacuum inlet, wherein the cutting cannula is disposed coaxially with the tissue receiving cannula, the cutting cannula being slidable axially along the tissue receiving cannula for cutting a tissue sample protruding into the tissue receiving opening when the cutting cannula slides past the tissue receiving opening;
    vacuum chamber walls defining a vacuum chamber configurable to be in fluid communication with the tissue receiving cannula lumen and the tissue receiving opening; and
    a trigger configured such that actuation of the trigger will cause the cutting cannula to slide axially along the tissue receiving cannula,
    wherein the cutting cannula extends into the vacuum chamber, and
    wherein the tissue receiving cannula and the cutting cannula are configured such that relative movement of one of the tissue receiving cannula and the cutting cannula with respect to the other moves the vacuum inlet into communication with the vacuum chamber, thereby placing the vacuum chamber in communication with the tissue receiving opening before the cutting cannula advances distally over the tissue receiving opening.

2. A tissue removal device, comprising:
    a tissue receiving cannula defining a tissue receiving opening near a distal end thereof and a tissue receiving cannula lumen in fluid communication with the tissue receiving opening formed in a sidewall of the tissue receiving cannula, the tissue receiving opening being configured to receive a tissue sample positioned adjacent the tissue receiving opening;
    a cutting cannula defining an open distal end and a cutting cannula lumen in fluid communication with the cutting cannula open distal end, wherein the cutting cannula is disposed coaxially with the tissue receiving cannula, the cutting cannula being slidable axially along the tissue receiving cannula for cutting a tissue sample protruding into the tissue receiving opening when the cutting cannula slides past the tissue receiving opening;
    vacuum chamber walls defining a vacuum chamber in fluid communication with the tissue receiving cannula lumen and the tissue receiving opening; and
    a trigger configured such that actuation of the trigger will cause the cutting cannula to slide axially along the tissue receiving cannula,
    wherein a vacuum chamber wall is mechanically connected to the cutting cannula, such that movement of the cutting cannula relative to the tissue receiving cannula will cause movement of the vacuum chamber wall, thereby expanding the vacuum chamber, and wherein the cutting cannula is configured to rotate while advancing distally relative to the tissue receiving cannula.

3. The tissue removal device of claim 1, wherein the tissue receiving cannula, the cutting cannula and the vacuum chamber walls are configured such that, after the vacuum chamber is expanded, the vacuum inlet is disposed in the vacuum chamber, such that vacuum generated in the vacuum chamber is delivered to the tissue receiving opening via the vacuum inlet and the cutting cannula lumen.

4. The tissue removal device of claim 1, further comprising a one way flow valve in fluid communication with the vacuum chamber.

5. The tissue removal device of claim 1, wherein the tissue receiving cannula is slidably disposed in the cutting cannula.

6. The tissue removal device of claim 1, wherein the cutting cannula is slidably disposed in the tissue receiving cannula.

7. A biopsy device, comprising:
   a cutting element having a proximal end, a distal end, and a vacuum inlet between the proximal and distal ends, the cutting element comprising
      a cannula having a lumen and a tissue receiving opening formed in a sidewall of the cannula for receiving a tissue sample positioned adjacent the tissue receiving opening, and
      an elongate cutter defining an axial lumen therethrough, the elongate cutter being disposed coaxially with the cannula and slidable axially along the cannula for cutting the tissue sample protruding into the tissue receiving opening when the elongate cutter slides past the tissue receiving opening; and
   a vacuum chamber,
   wherein the cannula and the cutter are configured such that relative movement of one of the cannula and the cutter with respect to the other moves the vacuum inlet into communication with the vacuum chamber, thereby placing the vacuum chamber in communication with the tissue receiving opening before the cutting cannula advances distally over the tissue receiving opening.

8. The biopsy device of claim 7, wherein the vacuum inlet is an opening formed in a sidewall of the elongate cutter.

9. A tissue removal device, comprising:
   a tissue receiving cannula defining a tissue receiving opening near a distal end thereof and a tissue receiving cannula lumen in fluid communication with the tissue receiving opening formed in a sidewall of the tissue receiving cannula, the tissue receiving opening being configured to receive a tissue sample positioned adjacent the tissue receiving opening;
   a cutting cannula defining an open distal end, a vacuum inlet, and a cutting cannula lumen in fluid communication with the cutting cannula open distal end and the vacuum inlet, wherein the cutting cannula is disposed coaxially with the tissue receiving cannula, the cutting cannula being slidable axially along the tissue receiving cannula for cutting a tissue sample protruding into the tissue receiving opening when the cutting cannula slides past the tissue receiving opening;
   a vacuum chamber disposed around-at least a portion of the cutting cannula,
   wherein the tissue receiving cannula and the cutting cannula are configured such that relative movement of one of the tissue receiving cannula and the cutting cannula with respect to the other moves the vacuum inlet into communication with the vacuum chamber, thereby placing the vacuum chamber in communication with the tissue receiving opening before the cutting cannula advances distally over the tissue receiving opening.

10. The biopsy device of claim 7, further comprising a vacuum seal disposed proximate the elongate cutter, wherein the vacuum seal is configured to selectively maintain vacuum in the vacuum chamber.

\* \* \* \* \*